US006589730B1

(12) United States Patent
Larocca et al.

(10) Patent No.: US 6,589,730 B1
(45) Date of Patent: *Jul. 8, 2003

(54) METHODS FOR IDENTIFYING PROTEIN-PROTEIN INTERACTIONS BY SELECTIVE TRANSDUCTION

(75) Inventors: David Larocca, Encinitas, CA (US); Andrew Baird, San Diego, CA (US); Paul Kassner, Hayward, CA (US)

(73) Assignee: Selective Genetics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/193,445

(22) Filed: Nov. 17, 1998

Related U.S. Application Data

(63) Continuation-in-part of application No. 09/141,631, filed on Aug. 28, 1998, now abandoned.
(60) Provisional application No. 60/057,067, filed on Aug. 29, 1997, now abandoned.

(51) Int. Cl.[7] ............................. C12Q 1/70; C12P 21/06
(52) U.S. Cl. ............................... 435/5; 435/6; 435/69.1; 435/69.8; 435/320.1; 435/DIG. 1; 435/DIG. 4; 435/DIG. 14; 435/DIG. 15; 435/DIG. 35; 536/23.1; 536/23.4; 536/25.32
(58) Field of Search ........................... 435/4.5, 7.1, 7.2, 435/7.21, 7.23, 7.72, 8, 172.1, 235.1, 320.1, 69.7, 69.1, 189, 252.3, DIG. 1, DIG. 3, DIG. 4, DIG. 14, DIG. 15, DIG. 22, DIG. 34, DIG. 35, DIG. 47; 536/23.1, 23.4, 25.32; 530/350

(56) References Cited

U.S. PATENT DOCUMENTS

| 5,733,731 A | 3/1998 | Schatz et al. ................. 435/6 |
| 5,955,275 A * | 9/1999 | Kamb ........................... 435/6 |
| 6,323,004 B1 | 11/2001 | Kang ........................ 435/69.1 |

FOREIGN PATENT DOCUMENTS

| WO | WO 92/20791 | 11/1992 |
| WO | WO 95/34648 | 12/1995 |
| WO | WO 97/00271 | 1/1997 |
| WO | WO 97/06435 | 2/1997 |
| WO | WO 98/05344 | 2/1998 |
| WO | WO 98/39482 | 9/1998 |
| WO | WO 99/10485 | 3/1999 |

OTHER PUBLICATIONS

Barry et al, Nature Medicine, 2(3), (Mar. 1996), 299–305.*
Larocca et al., "Targeted Transduction of Mammalian Cells Using a FGF2 Modified Filamentous Bacteriophage," *Cancer Gene Therapy* 4(6): Abstract No. O-46, p. S24, 1997.

Larocca et al., "Targeted Gene Delivery to Mammalian Cells Via Fibroblast Growth Factor (FGF–2) Display Phage," *Cancer Gene Therapy* 5(6): Abstract No. PD–31, p. S10, 1998.
Larocca et al., "Targeting Bacteriophage to Mammalian Cell Surface Receptors for Gene Delivery," *Human Gene Therapy* 9: 2393–2399, 1998.
Larocca et al., "Gene Transfer to Mammalian Cells Using Genetically Targeted Filamentous Bacteriophage," *FASEB J.* 13: 727–734, 1999.
Pasqualini and Ruosiahti, "Organ Targeting in vivo Using Phage Display Peptide Libraries," *Nature* 380:364–366, 1996.
Souriau et al., "A Simple Luciferase Assay for Signal Transduction Activity Detection of Epidermal Growth Factor Displayed on Phage," *Nucleic Acids Research* 25(8): 1585–1590, 1997.
Sosnowski et al., "Targeting DNA to Cells with Basic Fibroblast Growth Factor (FGF2)," *The Journal of Biological Chemistry* 271(52): 33647–33653, 1996.
Voiculescu, "Aspecte ale interrelatiilor bacteriofagi–celule cucariote" *Bacteriologia Virusologia, Parazitologia, Epidemiologia* XXII(3): 141–148, 1977 (+ English Translation).
"New Living Colors™ GFP Mammalian Vectors," *Clontechniques* XI(3): 20–22, 1996, http://www.clontech.com/archive/JUL96UPD/EGFP.html. [Accessed Nov. 25, 1998].
Dunn, "Mammalian cell binding and transfection mediated by surface–modified bacteriophage lambda," *Biochimie* 78: 856–861, 1996.
Goldman et al., "Targeted Gene Delivery to Kaposi's Sarcoma Cells via the Fibroblast Growth Factor Receptor," *Cancer Research* 57: 1447–1451, 1997.
Hart et al., "Cell Binding and Internalization by Filamentous Phage Displaying Cyclic Arg–Gly–Asp–containing Peptide," *The Journal of Biological Chemistry* 269(17): 12468–12474, 1994.
Hart et al., "Filamentous Phage For Cell Targeting And Gene Delivery," *Journal of Cellular Biochemistry Supplement* 18A: p. 225, Abstract No DZ 114, 1994.
Jespers et al., "λZLG6: a phage lambda vector for high–efficiency cloning and surface expression of cDNA libraries on filamentous phage," *Gene* 173: 179–181, 1996.

(List continued on next page.)

Primary Examiner—Padmashri Ponnaluri
(74) Attorney, Agent, or Firm—Seed Intellectual Property Law Group PLLC

(57) ABSTRACT

A method for identifying specific protein-protein (i.e., ligand/anti-ligand) interactions that internalize and are detected by transgene expression. A ligand displaying genetic package that carries a reporter or selectable marker and presents a ligand or putative ligand on its surface is utilized to screen cells displaying known or putative anti-ligands for the ability to successfully internalize the ligand displaying genetic package.

25 Claims, 11 Drawing Sheets

OTHER PUBLICATIONS

Russell, "Peptide–displaying phages for targeted gene delivery," *Nature Medicine* 2(3): 276–277, 1996.

Sawyer et al., "Methodology for selection of human antibodies to membrane proteins from a phage–display library," *Journal of Immunological Methods* 204: 193–203, 1997.

Spada and Plückthun, "Selectively infective phage (SIP) technology: A novel method for in vivo selection of interacting protein–ligand pairs," *Nature Medicine* 3(6): 694–696, 1997.

Yokoyama–Kobayashi and Kato, "Recombinant f1 Phage Particles Can Transfect Monkey COS–7 Cells by DEAE Dextran Method," *Biochemical And Biophysical Research Communications* 192(2): 935–939, 1993.

\* cited by examiner

SEQUENCE LISTING

```
<160> NUMBER OF SEQ ID NOS: 4

<210> SEQ ID NO 1
<211> LENGTH: 10
<212> TYPE: PRT
<213> ORGANISM: Unknown
<220> FEATURE:
<223> OTHER INFORMATION: Description of Unknown Organism:  A screened
      peptide, from a random peptide library, that binds
      and internalizes in a FGF receptor overproducing
      cell line

<400> SEQUENCE: 1

Phe Val Pro Asp Pro Tyr Arg Lys Ser Arg
  1               5                  10

<210> SEQ ID NO 2
<211> LENGTH: 10
<212> TYPE: PRT
<213> ORGANISM: Unknown
<220> FEATURE:
<223> OTHER INFORMATION: Description of Unknown Organism:  A screened
      peptide, from a random peptide library, that binds
      and internalizes in a FGF receptor overproducing
      cell line

<400> SEQUENCE: 2

Cys Gly Gly Gly Pro Val Ala Gln Arg Cys
  1               5                  10

<210> SEQ ID NO 3
<211> LENGTH: 10
<212> TYPE: PRT
<213> ORGANISM: Unknown
<220> FEATURE:
<223> OTHER INFORMATION: Description of Unknown Organism:  A screened
      peptide, from a random peptide library, that binds
      and internalizes in a FGF receptor overproducing
      cell line

<400> SEQUENCE: 3

Cys Leu Ala His Pro His Gly Gln Arg Cys
  1               5                  10
```

-continued

```
<210> SEQ ID NO 4
<211> LENGTH: 4
<212> TYPE: PRT
<213> ORGANISM: Unknown
<220> FEATURE:
<223> OTHER INFORMATION: Consensus nuclear localization sequence
<220> FEATURE:
<221> NAME/KEY: VARIANT
<222> LOCATION: (2)...(3)
<223> OTHER INFORMATION: Xaa = Any amino acid
<220> FEATURE:
<221> NAME/KEY: VARIANT
<222> LOCATION: (4)...(4)
<223> OTHER INFORMATION: Xaa = Lysine or Arginine

<400> SEQUENCE: 4

Lys Xaa Xaa Xaa
  1
```

METHODS FOR IDENTIFYING PROTEIN-PROTEIN INTERACTIONS BY SELECTIVE TRANSDUCTION

CROSS-REFERENCE TO RELATED APPLICATION

This application is a continuation-in-part of U.S. Ser. No. 09/141,631, filed Aug. 28, 1998, now abandoned; which application claims the benefit of priority from U.S. Provisional Application Ser. No. 60/057,067, filed Aug. 29, 1997, now abandoned.

TECHNICAL FIELD

This invention relates generally to screening for protein-protein interactions, and in particular, to identification of specific protein-protein interactions which lead to internalization of the protein-protein complex and transgene expression in the target cell.

BACKGROUND OF THE INVENTION

Bacteriophage expressing a peptide on its surface has been used to identify protein binding domains, including antigenic determinants, antibodies that are specifically reactive, mutants with high affinity binding, identify novel ligands, and substrate sites for enzymes. In its most common form, a peptide is expressed as a fusion protein with a capsid protein of a filamentous phage. This results in the display of the foreign protein on the surface of the phage particle. Libraries of phages are generated that express a multitude of foreign proteins. These libraries are bound to a substrate or cell that presents the binding partner of interest. This screening process is essentially an affinity purification. Bound phage are recovered, propagated, and the gene encoding the foreign protein may be isolated and characterized. This technology is commonly referred to as "phage display."

Through a process called "biopanning," the specific phage carrying a peptide or protein that interacts with a protein or other moiety on a solid phase can be identified and isolated. However, in some applications, binding or binding affinity is not the sole critical parameter. For example, in gene therapy, a gene sequence needs to be introduced into a cell. In preferred methods, the gene sequence is targeted to particular cells by way of a ligand/cell surface receptor interaction. Thus, the ligand must not only bind to the cells but must also be internalized. A native ligand that is internalized, when used in a system for gene therapy may not be efficiently internalized. For example, both FGF2 and EGF are internalizing ligands; however, of these two ligands, FGF (or polypeptides reactive with the FGF receptor) is currently preferred as a gene targeting ligand.

Phage libraries can be screened for internalizing ligands by biopanning on live cells and rescuing internalized phage from the cells after stripping off externally bound phage (e.g., acid elution). However, this method may result in recovery of undesired phage that bind very tightly or are only partially internalized. Moreover, phage that are internalized and subjected to proteases lose infectivity and can not be recovered. Accordingly, current methodologies are inadequate to determine the usefulness of ligands for gene therapy.

Further, identification of target cells or tissues that are able to internalize ligands and express a transgene would readily allow one to identify specific target cells for known or putative ligands as well as allow one to identify ligands for specific cell or tissue types. However, current methods of target cell identification are hampered by the same difficulties, as noted above, with regard to screening for internalizing ligands. Accordingly, current methodologies are inadequate to determine which cell or tissue types are useful targets for ligand mediated gene therapy.

Thus, current screening methods are inadequate for identifying cell or tissue types that bind and internalize known or putative ligands. The present invention discloses a ligand display method that identifies target cells or tissue types that bind internalizing ligands as well as identifying the specific ligands that internalize in the target cell or tissue, and further provides other related advantages.

SUMMARY OF THE INVENTION

Within one aspect of the present invention, a method of selecting internalizing ligand/anti-ligand pairs is presented, comprising: (a) contacting a ligand displaying genetic package(s) with a cell(s), wherein the package carries a gene encoding a detectable product which is expressed upon internalization of the package; and (b) detecting product expressed by the cell(s); thereby selecting ligand/anti-ligand pairs.

In another aspect, the invention provides a method of identifying a ligand or anti-ligand of an internalizing ligand/anti-ligand pair, comprising: (a) contacting one or more ligand displaying genetic packages with a cell(s), wherein each package carries a gene encoding a detectable product which is expressed upon internalization of the package, and wherein the cell(s) expresses an anti-ligand-receptor fusion protein on its surface; (b) detecting product expressed by the cell(s); and (c) recovering a nucleic acid molecule encoding an internalizing ligand and/or a nucleic acid molecule encoding an internalizing anti-ligand from the cell(s) expressing the product, and thereby identifying a ligand or anti-ligand of a internalizing ligand/anti-ligand pair.

In yet another aspect, the invention provides a method of identifying a ligand or anti-ligand of an internalizing ligand/anti-ligand pair, comprising: (a) contacting one or more ligand displaying genetic packages with a cell(s), wherein each package carries a gene encoding a detectable product which is expressed upon internalization of the package, and wherein the cell(s) expresses an anti-ligand-receptor fusion protein on its surface; (b) incubating the cell(s) under selective conditions; and (c) recovering a nucleic acid molecule encoding an internalizing ligand and/or a nucleic acid molecule encoding an internalizing anti-ligand from the cell(s) which grow under the selective conditions; thereby identifying a ligand or anti-ligand of a internalizing ligand/anti-ligand pair, comprising.

In yet another aspect, a method is provided for a high throughput method of identifying a ligand or anti-ligand of an internalizing ligand/anti-ligand interactions, comprising: (a) contacting one or more ligand displaying genetic packages with a cell(s) in an array, wherein each package carries a gene encoding at least one detectable product which is expressed upon internalization of the package; and (b) detecting product(s) expressed by the cell(s) in the array, and thereby identifying a ligand or anti-ligand of a internalizing ligand/anti-ligand interactions. In one embodiment, the array contains cells expressing a library of anti-ligand-receptor fusion proteins. In another embodiment, the ligand displaying package comprises a library of ligand displaying packages.

In preferred embodiments, the ligand displaying genetic package comprises a bacteriophage. The bacteriophage are filamentous phage or lambdoid phage in other preferred embodiments. In some embodiments, the bacteriophage carries a genome vector.

In other embodiments, the library is a cDNA library, an antibody gene library, a random peptide gene library, or a mutein library. In other preferred embodiments, the detectable product is selected from the group consisting of green fluorescent protein, β-galactosidase, secreted alkaline phosphatase, chloramphenicol acetyltransferase, luciferase, human growth hormone and neomycin phosphotransferase.

In other embodiments, the cells may be isolated by flow cytometry, for example. In further embodiments, the methods further comprise recovering a nucleic acid molecule encoding the ligand and/or a nucleic acid molecule encoding the anti-ligand from the cell(s) expressing the product.

These and other aspects of the present invention will become evident upon reference to the following detailed description and attached drawings. In addition, various references are set forth below which describe in more detail certain procedures or compositions (e.g., plasmids, etc.), and are therefore incorporated herein by reference in their entirety.

BRIEF DESCRIPTION OF THE DRAWINGS

FIG. 1A depicts the parent phage vector with wild type pIII coat protein. The base vector is M13 genome with ampicillin resistance ($Amp^R$) gene and GFP expression cassette inserted into the intergenic region between pIV and pII (MEGFP3). The MEGFP3 vector contains the following elements: ori-CMV, SV40 replication origin and CMV promoter; EGFP, enhanced green fluorescent protein gene; BGH, and a bovine growth hormone polyadenylation sequence. FIG. 1B represents the FGF-pIII fusion display phage (MF2/1G3).

FIG. 3A depicts the amount of phage protein detected using both the empty MEGFP3 vector and the FGF2 fusion construct (FGF2-MEGFP). FIG. 3B depicts the amount of FGF2 detected on the phage having the fusion construct.

DETAILED DESCRIPTION OF THE INVENTION

As noted above, the present invention provides a method of ligand display that identifies and/or selects for cells or tissue types that bind ligands as well as allowing identification of protein ligands that bind and internalize on the basis of expression of a transgene that is carried on a ligand displaying genetic package construct. While it should be understood that a variety of ligand display methods may be utilized (e.g., phage display, RNA-peptide fusions, and ligand displaying bacteria), the present invention uses bacteriophage ligand display to exemplify the various embodiments.

Figure 1A:
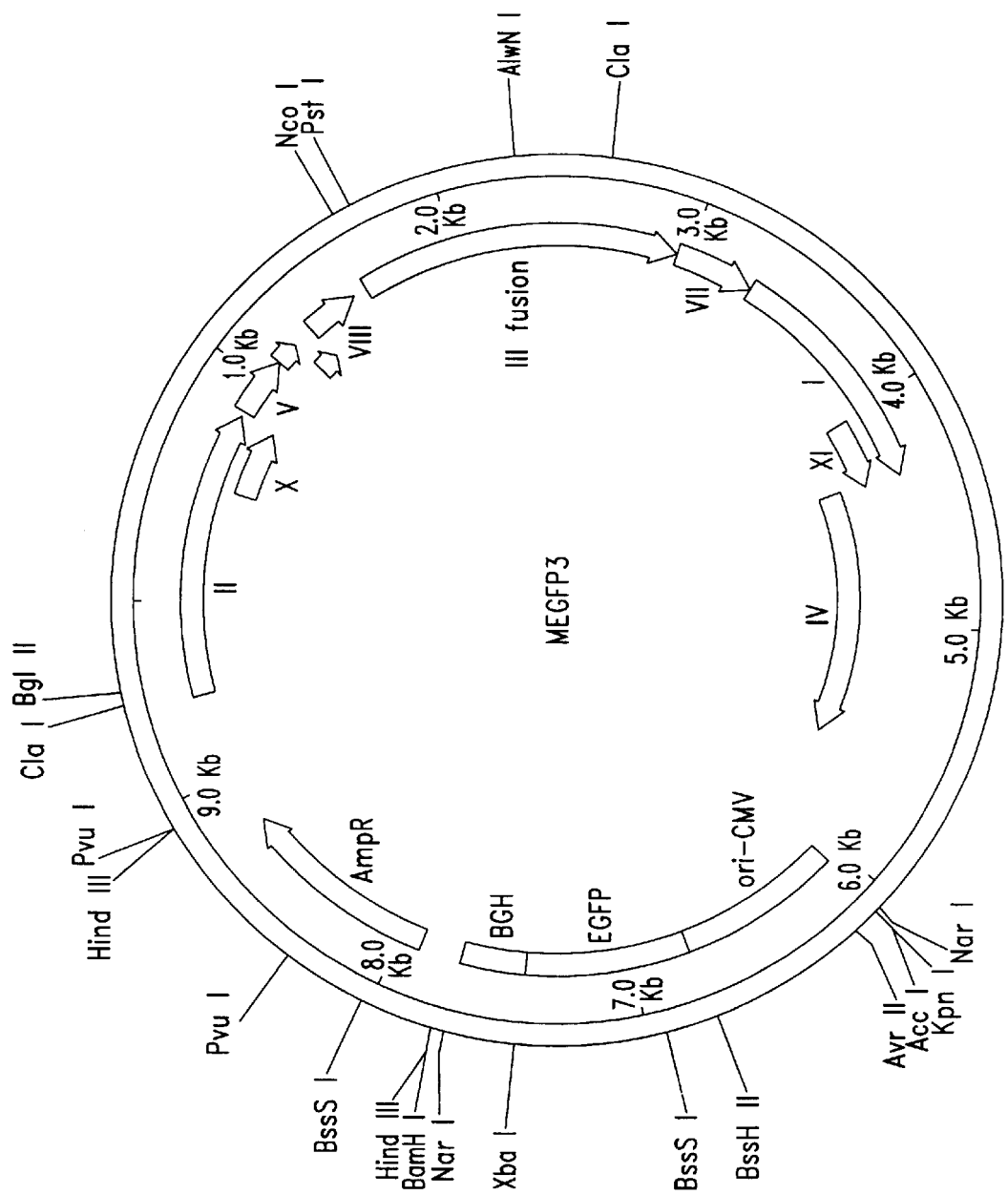
FIGS. 1A and 1B are schematic representations of phage vectors for mammalian cell transduction.

Briefly, in one embodiment of the present invention, a library of antibodies, cDNAs, or genes encoding random peptides is cloned into a coat protein (e.g., gene III protein of filamentous phage) of a bacteriophage. The phage genome also contains an "expression cassette" encoding a transgene placed downstream from a cell promoter that is active in the cells to be infected (FIG. 1A). The transgene is generally a selectable gene product and/or a detectable marker. Phage are contacted with test cells and expression of the transgene is monitored or selected. Phage that internalize will confer the phenotype of the transgene, such as drug resistance or expression of a fluorescing protein. The cells may be isolated on the basis of transgene expression. For example, when the transgene is a drug resistance gene, cells are grown in the presence of the drug, such that only those cells receiving and expressing the transgene are propagated. The gene(s) that are fused with the coat protein and that promoted cell binding and internalization are recovered from the selected cells by a suitable method.

I. DISPLAY PACKAGES

A variety of displaying genetic packages may be used within the context of the present invention. A "ligand displaying genetic package" as used herein, refers to any package which comprises a peptide/protein ligand and carries an expressible nucleic acid molecule for detection, once internalized in the target cell. For example, display may be by a virus, RNA-peptide fusions, bacteriophage, bacteria, or similar system (See, Kay, Phage Display of Peptides and Proteins, pages 151–193, *Academic Press*, 1996). Preferred methods utilize bacteriophages. Such phage include the filamentous phages, lambda, T4, MS2, and the like. A preferred phage is a filamentous phage, such as M13 or f1.

Phage that present the foreign protein or peptide as a fusion with a phage coat protein are engineered to contain the appropriate coding regions. A variety of bacteriophage and coat proteins may be used. Examples include, without limitation, M13 gene III, gene VIII; fd minor coat protein pIII (Saggio et al., *Gene* 152: 35, 1995); lambda D protein (Sternberg and Hoess, *Proc. Natl. Acad Sci. USA* 92: 1609, 1995; Mikawa et al., *J. Mol. Biol.* 262: 21, 1996); lambda phage tail protein pV (Maruyama et al., *Proc. Natl. Acad. Sci. USA* 91: 8273, 1994; U.S. Pat. No. 5,627,024); fr coat protein (WO 96/11947; DD 292928; DD 286817; DD 300652); φ29 tail protein gp9 (Lee, *Virol.* 69: 5018, 1995); MS2 coat protein; T4 small outer capsid protein (Ren et al., *Protein Sci.* 5: 1833, 1996), T4 nonessential capsid scaffold protein IPIII (Hong and Black, *Virology* 194:481, 1993), or T4 lengthened fibritin protein gene (Efimov, *Virus Genes* 10:173, 1995); PRD-1 gene III; Qβ3 capsid protein (as long as dimerization is not interfered with); and P22 tailspike protein (Carbonell and Villaverde, *Gene* 176:225, 1996). Techniques for inserting foreign coding sequence into a phage gene are well known (see e.g., Sambrook et al., *Molecular Cloning: A Laboratory Approach*, Cold Spring Harbor Press, NY, 1989; Ausubel et al., *Current Protocols in Molecular Biology*, Greene Publishing Co., NY, 1995).

In the preferred filamentous phage system, a wide range of vectors are available (see, Kay et al., *Phage Display of*

*Peptides and Proteins: A Laboratory Manual*, Academic Press, San Diego, 1996). The most common vectors accept inserts in gene III or gene VIII. Furthermore, the foreign gene can be inserted directly into the phage genome or into a phagemid vector. Methods of propagation of filamentous phage and phagemids are well known.

Filamentous phage vectors generally fall into two categories: phage genome and phagemids. Either type of vector may be used within the context of the present invention. Many such commercial vectors are available. For example, the pEGFP vector series (Clontech; Palo Alto, Calif.), M13mp vectors (Pharmacia Biotech, Sweden), pCANTAB 5E (Pharmacia Biotech), pBluescript series (Stratagene Cloning Systems, La Jolla, Calif.) and others may be used. One particularly useful commercial phagemid vector is pEGFP-N1, which contains a green fluorescent protein (GFP) gene under control of the CMV immediate-early promoter. This plasmid also includes an SV40 origin of replication to enhance gene expression by allowing replication of the phagemid to high copy number in cells that make SV40 T antigen.

Other vectors are available in the scientific community (see e.g., Smith, in *Vectors: A Survey of Molecular Cloning Vectors and their Uses*, Rodriquez and Denhardt, eds., Butterworth, Boston, pp 61–84, 1988) or may be constructed using standard methods (Sambrook et al., *Molecular Biology: A Laboratory Approach*, Cold Spring Harbor, N.Y., 1989; Ausubel et al., *Current Protocols in Molecular Biology*, Greene Publishing, NY, 1995) guided by the principles discussed below.

The source of the ligand (e.g., gene, gene fragment or peptide encoding sequence) may be for example, derived from a cDNA library, antibody library or random peptide library. Alternatively, the ligand may be from a library of random or selective mutations of a known ligand. In an additional alternative, the ligand may be from a library of known receptor binding agents. For example, the library may contain a subset of peptides known to bind the FGF or EGF receptor, but that have unknown gene delivery and expression characteristics (i.e. transduction capacity).

When a cDNA library is used, the starting cDNA is synthesized from mRNA isolated from the source tissue or cell line from which the desired ligand originates. cDNA is then amplified using primers containing sequences of appropriate restriction enzyme sites for insertion into the desired vector. Alternatively, commercially available cDNA libraries (e.g., Clontech; Palo Alto, Calif.) may be amplified for insertion into the vector.

Similarly, libraries of antibody fragments can be made from mRNA isolated from the spleen cells of immunized animals (immunized for example with whole target cells or membranes) or subcloned from existing antibody libraries from immunized or naive animals. Random peptides are subcloned from libraries that are commercially available (New England Biolabs; MA) or can be synthesized and cloned using previously described methods (see, Kay et al., supra).

Phage display libraries of random or selective mutations of known ligands for improved gene delivery are performed in the same manner as described for screening random peptide libraries such libraries are referred to herein as a "mutein library" (i.e., a library of selective or random mutations). Random mutations of the native ligand gene may be generated using DNA shuffling as described by Stemmer (Stemmer, *Nature* 370: 389–391, 1994). Briefly, in this method, the ligand is amplified and randomly digested with DNase I. The 50–300 base pair fragments are reassembled in an amplification performed without primers and using Taq DNA polymerase or similar enzyme. The high error rate of this polymerase introduces random mutations in the fragments that are reassembled at random thus introducing combinatorial variations of different mutations distributed over the length of the gene. Error prone amplification may alternatively be used to introduce random mutations (Bartell and Szostak, *Science*, 261:1411, 1993). The ligand may be mutated by cassette mutagenesis (Hutchison et al., in *Methods in Enzymology* 202:356–390, 1991), in which random mutations are introduced using synthetic oligonucleotides and cloned into the ligand to create a library of ligands with altered binding specificities. Additional mutation methods can be used. Some additional methods are described in Kay et al., supra. Further, selective mutations at predetermined sites may be performed using standard molecular biological techniques (Sambrook et al., *Molecular Cloning: A Laboratory Manual*, Cold Spring Harbor Press, 1989).

If a cDNA library cannot be generated because, for example, the source of the desired ligand is not available or is unknown, random peptide libraries or a cDNA library from placenta may be used as a starting point for screening. Methods for construction of random peptide libraries may be found, for example, in Kay et al., supra. Briefly, the random peptides are encoded by DNA assembled from degenerate oligonucleotides and inserted into one of the bacteriophage vectors described herein. Several different strategies may be used to generate random peptides. For example, triplets of NNN, wherein each N is an equimolar representation of all four nucleotides, will generate all 20 amino acids (as well as 3 stop codons). Alternative strategies use NN(G/T) and NN(G/C), which results in 32 codons that encodes all 20 amino acids and only 1 stop codon. Other strategies utilize synthesis of mixtures of trinucleotide codons representing all 20 amino acids and no stop codons. Once the oligonucleotides are synthesized, they are assembled as double strands by a variety of schemes, one of which involves synthesis of the complementary strand (see Kay et al., supra).

In addition to the ligand/coat protein fusion, the vector contains a gene whose product can be detected or selected for. As referred to herein, a "reporter" gene is one whose product can be detected, such as by fluorescence, enzyme activity on a chromogenic or fluorescent substrate, and the like or selected for by growth conditions. Such reporter genes include, without limitation, green fluorescent protein (GFP), β-galactosidase, chloramphenicol acetyltransferase (CAT), luciferase, neomycin phosphotransferase, secreted alkaline phosphatase (SEAP), and human growth hormone (HGH). Selectable markers include drug resistances, such as neomycin (G418), hygromycin, and the like.

The marker gene is in operative linkage with a promoter. Any promoter that is active in the cells to be transfected can be used. The vector should also have a viral origin of replication and a packaging signal for assembling the vector DNA with the capsid proteins.

Most applications of the present invention will involve transfection of mammalian cells, including human, canine, feline, equine, and the like. The choice of the promoter will depend in part upon the targeted cell type. Promoters that are suitable within the context of the present invention include, without limitation, constitutive, inducible, tissue specific, cell type specific, temporal specific, or event-specific, although constitutive promoters are preferred.

Examples of constitutive or nonspecific promoters include the SV40 early promoter (U.S. Pat. No. 5,118,627), the SV40 late promoter (U.S. Pat. No. 5,118,627), CMV early gene promoter (U.S. Pat. No. 5,168,062), bovine papilloma virus promoter, and adenovirus promoter. In addition to viral promoters, cellular promoters are also amenable within the context of this invention. In particular, cellular promoters for the so-called housekeeping genes are useful (e.g., β-actin). Viral promoters are generally stronger promoters than cellular promoters.

In preferred embodiments, the phage has an origin of replication suitable for the transfected cells. Viral replication systems, such as EBV ori and EBNA gene, SV 40 ori and T antigen, or BPV ori, may be used. Other mammalian replication systems may be interchanged. As well, the replication genes may cause high copy number. Expression of therapeutic genes from the phage genome may be enhanced by increasing the copy number of the phage genome. In one method, the SV40 origin of replication is used in the presence of SV40 T antigen to cause several hundred thousand copy number. The T antigen gene may be already present in the cells, introduced separately, or included in the phage genome under the transcriptional control of a suitable cell promoter. Other viral replication systems for increasing copy number can also be used, such as EBV origin and EBNA.

In other embodiments, peptides or other moieties that allow or promote the escape of the vectors (and any molecule attached thereto or enclosed therein) from the endosome are incorporated and expressed on the surface of the bacteriophage. Such "other moieties" include molecules that are not themselves peptides but which have the ability to disrupt the endosomal membrane, thereby facilitating the escape of the vector, and molecules that otherwise mimic the endosomal escape properties of the within-described peptide sequences (see, e.g., published PCT Application No. WO96/10038, the disclosure of which is incorporated by reference herein).

Peptide sequences that confer the ability to escape the endosome are particularly preferred. Such sequences are well known and can be readily fused covalently or genetically to a coat protein, such as gene III or gene VIII of filamentous phage. Although fusion of one or more peptide sequences to a coat protein is described herein as a preferred embodiment, it should be understood that other methods of attachment—and other moieties besides peptides—are useful as disclosed herein.

Thus, an example of a dual display filamentous phage presents a ligand (e.g., FGF) as a fusion to gene III and an endosomal escape peptide fused to gene VIII. The locations of the ligand and escape sequences are interchangeable. Escape sequences that are suitable include, without limitation, the following exemplary sequences: a peptide of Pseudomonas exotoxin (Donnelly, J. J., et al., *PNAS* 90:3530–3534, 1993); influenza peptides such as the HA peptide and peptides derived therefrom, such as peptide FPI3; Sendai Virus fusogenic peptide; the fusogenic sequence from HIV gp1 protein; Paradaxin fusogenic peptide; and Melittin fusogenic peptide (see WO 96/41606).

Another sequence that may be included in a vector is a sequence that facilitates trafficking proteins into the nucleus. These so-called nuclear translocation or nuclear localization sequences (NLS) are generally rich in positively charged amino acids. Because the carboxyl terminus of gene VIII protein of filamentous phage already carries a positive charge, increased charge and likeliness of nuclear transport may be enhanced by fusing known mammalian cell NLS sequences to the gene VIII protein. NLS fusions to other coat proteins of filamentous phage may be substituted.

Examples of NLS sequences include those resembling the short basic NLS of the SV40 T antigen; the bipartite NLS of nucleoplasmin; the ribonucleoprotein sequence A1; the small nuclear ribonucleoprotein sequence U1A, and human T-lymphocyte virus-1Tax protein. Other useful NLS sequences include the HIV matrix protein NLS; and the nuclear translocation components importin/hSRP1 and Ran/TC4; the consensus sequence KXX(K/R) flanked by Pro or Ala; the nuclear translocation sequence of nucleoplasmin; or the NLS from antennapedia (see WO 96/41606).

As described herein, the library is then propagated in the display phage by transfection of a suitable bacteria host (e.g., DH5αF' for filamentous phages), and growing the culture, with the addition of a replication-competent helper virus if necessary, overnight at 37° C. The phage particles are isolated from the culture medium using standard protocols.

Infection of mammalian cells with phage is performed under conditions that block entry of wild type phage into cells (Barry et al., *Nature Med.* 2:299–305, 1996). Phage are added directly to cells, typically at titers of $\leq 10^{12}$ CFU/ml in a buffer, such as PBS with 0.1% BSA or other suitable blocking agents, and allowed to incubate with the cells at 37° C. or on ice. The amount of phage added to cells will depend in part upon the complexity of the library. For example, a phage display library containing $10^5$ members has each member represented $10^6$ times in 1 ml of a typical phage titer of $10^{11}$ colony forming units/ml.

II. DETECTION/SELECTION OF TRANSGENE EXPRESSION

The phage display library is ultimately screened against the target tissue or cell line. Screening can be performed in vitro or in vivo. While combinatorial screening methods have been performed in the past, these methods are unable to determine the transduction capability of the displayed ligand (see, U.S. Pat. No. 5,733,731, incorporated herein by reference). The criteria for a positive "hit" in the present invention is that the phage must be able to bind, be internalized, and express the genomic DNA containing the reporter gene in the target cell. In this regard, it is believed that the phage should bind, internalize, translocate to the nucleus, uncoat and replicate, in order to express the gene. Thus, only phage that express a reporter gene are selected.

The test cells may be any cells that express a receptor of choice or are a cell type or source for which gene therapy is destined. Thus, in some instances, the receptor may be unknown. In such cases, the selection method can be used to isolate a ligand for a receptor without a known ligand (orphan receptor) such as erbB3. Briefly, the orphan receptor is cloned into a mammalian expression vector that also contains a selectable drug resistance gene and transfected into mammalian cells, such as COS cells. Stable transfectants that overproduce the orphan receptor are selected by cultivation in the appropriate drug. This receptor-transformed COS cell line is then used as the cell line for selection of ligand-displaying phage.

Tissue-specific or tumor-specific ligands can be selected by pre-absorption of the phage library against normal or non-targeted tissues of cell cultures. The selection process can also be applied in vivo by injecting the library into tumor-bearing mice. The tumor is removed from the mouse 48–72 h after injection. A cell suspension is prepared and phage genome bearing cells selected by one of the methods described herein. The gene whose product allows entry and expression of the phage genome is then isolated from the drug resistant cell colonies.

Screening may be performed directly against the target cells with no pre-screening or pre-enrichment. In one aspect, the present invention provides a method of identifying target cells or tissues for known or putative ligands. In this regard, phage display may be used to display a library of known or putative ligands (e.g., peptides, antibody fragments and the like) and screen singular tissues or cell types, or pools of tissues or cell types, thereby identifying target cells or tissues which are effectively transduced by a ligand. As used herein, "pool" refers to two or more cell types or tissue types. In one embodiment, known ligands are presented on a ligand displaying genetic package to a pool of a variety of cell or tissue types and transgene expression is monitored. In a further embodiment, putative ligands are used to screen a pool of a variety of cell or tissue types for transduction ability. In this regard ligands may be recovered and identified which efficiently transduce a particular tissue or cell type. Identification of cell specific ligands could greatly improve existing vectors for therapeutic gene delivery by targeting specific cells thus reducing toxicity and allowing vectors to be administered systemically.

Such cell type or tissue-type screening provides for selection that requires biological interaction rather than simple binding and does not require recovery of infective phage. In addition, cell surface receptors need not be identified and purified for the screening to be effective. A further aspect of the present invention is that it can be easily adapted to high throughput applications for screening a variety of cell types or tissues and/or for screening libraries of putative ligands against libraries of putative receptors/binding partners (i.e., anti-ligands) which lead to transgene expression (see infra). In this regard, screening of a variety of ligand/cell interactions could be performed, including, for example, pathogen/host interactions, ligand/receptor, etc.

In one aspect, the present invention may be utilized to identify a variety of protein-protein interactions. In particular, a set of unknown proteins/peptides may be selected based upon interaction with another set of known or unknown proteins/peptides (e.g., random peptides, cDNA libraries, or antibody gene libraries). In one embodiment, putative ligands are displayed on the surface of filamentous phage that carry a reporter gene. These display phage are contacted with a cell line displaying a putative anti-ligand (protein/peptide) on its surface as a receptor fusion protein, such that binding of successful detection of the reporter gene requires binding of the phage display ligand and the cell surface displayed anti-ligand, as well as internalization and transgene expression. Such screening can be utilized in a variety of methods, for example, a known ligand may be screened against a library of potential anti-ligands, a library of unknown ligands may be screened against a known protein/peptide anti-ligand, and two libraries of peptides/proteins may be screened against each other to identify ligand/anti-ligand interactions (protein-protein).

A ligand/anti-ligand pair refers to a complementary/anti-complementary set of molecules that demonstrate specific binding, generally of relatively high affinity. Exemplary ligand/anti-ligand pairs include an antibody and its ligand as well as ligand/receptor binding. While it should be understood that the designation of either component of the above mentioned ligand/anti-ligand pairs as either a ligand or anti-ligand is arbitrary, when necessary to specify a particular component, a "ligand", as used herein, is meant to describe peptides or proteins displayed on a genetic package carrying an expressible transgene. Further, when necessary to define anti-ligand with specificity, an "anti-ligand", as used herein, demonstrates high affinity and is expressed on the surface of the target cell to be monitored for transgene expression.

Any cell surface receptor may be used as the fusion construct for the cell surface displayed anti-ligand. However, in a preferred embodiment, the extracellular domain of the receptor is replaced with the putative anti-ligand. Construction of such fusions is routine in the art given that sequences as well as the extracellular intracellular domains of numerous receptors are known and available in the art. Komesli et al., *Eur. J. Biochem* 254(3):505–513, 1998; Naranda et al., *Proc. Natl. Acad. Sci. USA* 94(21):11692–11697, 1997; Rutledge et al., *J. Biol. Chem.* 266(31):21125–21130, 1991; Lemmon et al., *Embo J.* 16(2):281–294, 1997; Foehr et al., *Immunol. Cell Biol* 76(5):406–413, 1998. Exemplary fusion constructs include, for example, anti-ligand-FGF receptor or anti-ligand-EGF receptor constructs.

In a further embodiment, a large pool of cDNAs may be tested by transfecting into a large number of mammalian cells (e.g., COS cells). Ligand displaying phage are exposed to the transfected cells and positive cells identified by either drug selection or detection of an expressed transgene (e.g., GFP sorted by FACs). PCR may be performed on single cells to identify ligand/anti-ligand binding pairs. In this regard PCR primers directed to the known portion of the fusion construct may be used. For example, for phage display using pIII to display the ligand, the PCR primer will be directed to the pIII gene, while in order to identify the anti-ligand, the PCR primer will be directed to the surface membrane protein (e.g., a receptor domain) encoding portion of the fusion construct. Alternatively, the plasmids within positive cells may be rescued by Hirt supernatant method and separated from phage DNA by gel electrophoresis or chromatography. (Kay et al., supra). The selected cDNA plasmids may then be used to retransform bacteria. New plasmid DNA is prepared and used for additional rounds of screening by transfection into the cells and phage contact.

In a further embodiment, known or putative ligand-display phage may be used to screen a panel of cells that each express a potential target receptor. The source of the target receptor may be a known (i.e. cloned) receptor cDNA, or a collection of putative receptor cDNAs. For example, the putative receptor cDNAs may be identified from an epitope-tagged cDNA library as cDNAs that encode proteins that appear on the surface of cells. (see, Sloan et al., *Protein Expression and Purification* 11:119–124, 1997). Such cDNAs are inserted into an appropriate mammalian expression vector and transfected into a host cell. Preferably the host cell is eukaryotic, and more preferably the host cell is mammalian. The expression of the cDNA may be either stable or transient. Following expression the cells are contacted with the ligand-display phage and monitored for transgene expression (e.g., drug resistance, GFP, or other detectable product). One skilled in the art would recognize that identification of cell or tissue types as described above, in addition to using ligand display phage, could also performed by utilizing other ligand displaying means, such as RNA-peptide fusions as described by Roberts and Szostak (*Proc. Nat. Acad. Sci. USA* 94:12297–12302, 1997), other phage types, or on bacteria.

Pre-screening or pre-enrichment may be used and can be especially helpful when either too few or too many hits are observed. Enrichment for cell binding may improve detectability if no hits are found in the initial screen. A prescreen to remove phage that bind non-specific cells surface proteins may reduce non-specific hits if there are too many initial hits. For example, infection of $10^7$ target cells is performed with about $10^{11}$ phage, however a variety of cell density and phage titer ranges are useful. The cells are incubated for at least 2 hours in PBS/BSA and washed extensively (Barry et al., *Nature Med.* 2:299–305, 1996). The cells are incubated in media at 37° C. for 48–96 hours and then detected or selected on the basis of expression of the reporter gene.

Assays for each of these reporter gene products are well known. For example, GFP is detected by fluorescence microscopy or flow cytometry, SEAP is detected in medium using a fluorescent substrate (Clontech; Palo Alto, Calif.), human growth hormone may be detected in medium by a simple and sensitive radioimmune assay (Nichols Institute; CA). Western blotting and ELISA may also be used to immunologically detect and measure the presence of reporter gene product. Alternatively, the message for the reporter gene is detected using RNase probe protection or fluorescent probe hybridization. For isolation of the phage vector DNA and insert, any technique that can identify and isolate the cells expressing detectable marker product may be used. Flow cytometry, in particular, is well suited for detecting fluorescence in or on a cell and isolating that cell. Further, flow cytometry is well suited for high throughput methodologies when necessary to isolate individual cells or groups of cells that express a reporter gene.

When the reporter gene is a selectable marker, the cells are grown in selective conditions. Depending upon the marker, the conditions may be a particular growth temperature, addition of a drug, or the like. In the examples provided herein, the selectable marker is neomycin transferase, which confers G418 resistance on mammalian cells. Briefly, the cells are grown in the presence of G418 for 7–14 days or until resistant colonies are visible microscopically. Colonies are picked, and phage vector DNA recovered, conveniently as amplification of the insert.

Alternatively, multiple rounds of infection and selection are performed to reduce the complexity of the infecting phages. For example, drug-resistant colonies are pooled and the selected inserts amplified and cloned back into the phage display vector for a new round of infection. When the reporter is fluorescent, flow cytometry can be used to select the strongest fluorescing cells to select the most highly efficient gene delivery ligands. More stringent screening conditions also include higher selective drug concentrations. At the completion of a selection process, representative phage clones may be subjected to DNA sequence analysis to further characterize gene delivery ligands.

In a further aspect, high throughput screening methodologies, such as screening libraries by sub-selection of pools, may be utilized to identify ligands. Briefly, phage stocks containing a variety of members, as individual plaques, may be used in combination with an array to identify potential internalizing ligands. For example, a stock of bacteriophages containing library members may be divided into subset pool stocks such that each stock contains about $10^2$ to about $10^3$ members. Each stock solution is then screened utilizing an array (e.g., multiwell plates containing target cells). Upon detection of a reporter gene the phage stock may be sub-divided again and screened repeatedly until the phage which contains the internalizing ligand is identified. Alternatively, those of skill in the art will appreciate that the array may contain a variety of cell types which are capable of being screened with one or more phage libraries, of which may also include a variety of reporter genes (if so desired). For example, a variety of alternatively colored fluorescent protein expression vectors are available which can be used as reporter genes to provide multiplexing capability (Clonetech, Palo Alto, Calif.). Accordingly, rapid identification of those cells which internalize the bacteriophage and/or libraries that contain internalizing ligands for a specific cell type, may be identified. Utilizing both a variety of bacteriophage libraries as well as a variety of cell types, would allow for a high throughput method of determining subsets of libraries that contain ligands for specific cell types, simultaneously. Array's for binding biomolecules are known in the art and therefore could be adapted to utilize the phage screening methodology of the present invention, see, e.g., PCT Application No. WO 95/11755, PCT Application No. WO 95/35505, U.S. Pat. No. 4,591,570. In addition, affinity based biosensors such as a BIACORE™ instrument, available commercially from Biacore AB, Uppsula, Sweden, may be used to immobilize phage or cells for high throughput screening.

Moreover, while commonly used high throughput methodologies which utilize live cells are typically performed on arrays of 6 to 96 well plates, the current invention may also be carried out using cellular micro-arrays such as those described by U.S. Pat. No. 5,776,748. Briefly, such arrays may be manufactured such that designated areas of the array bind a defined number of cells or size of tissue. For example, the arrays can be constructed such that they bind only a single cell. Therefore, an array of single cells may be constructed with a variety of cell or tissue types. Because the size of the cell binding islands on the array may be chosen such that no more than one cell may bind on any given island, because the locations and geometric pattern of the islands may be predetermined, and because the cells will remain at fixed locations during assaying, cellular micro-arrays can provide for a high efficiency and high throughput method of assaying for internalizing ligands, anti-ligands, or target cells or tissues.

In a preferred embodiment flow cytometry is utilized, the cells are identified and counted by an automated detector unit. Because the locations and geometric patterns of the islands are predetermined, the detector can be designed or programmed to take measurements specifically at those locations. Therefore, identification of individual cells which have been successfully transduced by a ligand displaying genetic package carrying a nucleic acid molecule which encodes a detectable product is easily accomplished. In some embodiments, cells transduced by a ligand displaying genetic package carrying a nucleic acid molecule which encodes a selectable marker may be first selected on the basis of the appropriate sensitivity or resistance and then plated as individual cells and further selected or characterized by the methods described herein. In particular, selection may be employed prior to plating on the plates to isolate transformed or transfected cells and then the cells may be assayed in situ.

In addition, when using fluorescence assays, a detector unit may be placed above the plate or, if the plate is translucent, below the plate. In the case of transmission spectrophotometric assays, a translucent plate is used, a source of electromagnetic radiation is placed on one side of the plate and a detector unit on the other. Because of the small distances between individual isolated cells permitted by the present invention, detectors employing fiber optics are particularly preferred. Such sources of electromagnetic radiation and such detectors for electromagnetic transmission, reflection or emission are known in the applicable art and are readily adaptable for use with the invention disclosed herein.

Screening in vivo may be performed similar to methods for targeting organs or xenograft tumors using phage displayed peptides (Pasqualini et al., *Nature Biotech.* 15: 542–546, 1997; Pasqualini et al., *Nature* 380: 364–366, 1996), except that the tissues, organs, or tumors are examined for reporter gene expression instead of the presence of phage. Briefly, a phage display library is injected intravenously into animals, generally mice, and organs or tumor samples are tested for reporter gene function at 48–96 hours after injection. Tumor cells may be cultured in selective conditions or sorted by flow cytometry or other method to enrich for cells that express the phage transducing gene. The ligand encoding sequences can be amplified from selected cells as described above. As in in vitro screening, repeated rounds of infection and rescreening, alone or in combination with increased screening stringency, may be used to obtain the most efficient gene delivery ligands.

Specificity may also be examined in vitro using a panel of non-targeted and targeted cell lines and detecting expression of the phage transducing gene. Competition studies with free ligand or a neutralizing antibody to the ligand or receptor are used to confirm specific entry of phage via the ligand receptor complex. Alternatively, the cloned receptor for the ligand can be overexpressed in a cell line that normally does not express that receptor. Phage internalization and expression into the stable transfectants expressing the receptor but not the parent cell line indicates the specificity of the ligand for its receptor on receptor bearing cells.

Ligands that are identified as gene targeting ligands using the selection strategies described herein may be further tested for specificity by reporter gene expression in target and non-target cells and tissues. The ligand may also be tested in a variety of gene delivery methods, such as ligand-polylysine/DNA complexes (Sosnowski et al., *J. Biol. Chem.* 272:33647–33653, 1996) or retargeted adenovirus gene delivery (Goldman et a., *Cancer Research* 57:1447–1451, 1997).

The specificity of the targeting ligand may alternatively be determined in vivo by biodistribution analysis using one of the reporter genes described herein, such as luciferase. At various time points, mice injected with the ligand displaying phage are sacrificed and tissues examined for the presence of phage in non-targeted tissues by immunohistochemistry, an enzymatic assay that detects reporter product activity, or the like.

III. USES

The methods described herein are designed to select cDNAs, Fabs, sFv, random peptides, and the like for discovery of new ligands or anti-ligands. They can also be used to select mutated and gene-shuffled versions of known ligands for targeting ability.

These ligands may have increased transduction efficiency (as measured by an increase in the percentage of infected cells that express the reporter gene); increased expression of the reporter gene (as measured by intensity of reporter gene expression) in the phage transduced cells; increased specificity of transduction for target cells (as measured for ligand specificity); increased stability of the ligand (as measured by ability to target the ligand in vivo to tumor cells); increased affinity for receptor (e.g., removing dimerization requirements for ligands that dimerize); elimination of the need for cofactors (e.g., development of an FGF variant that binds with high affinity to the FGF receptor but not to heparin); altered specificity for receptor subtypes (e.g., an FGF variant that reacts with only one of the four FGF receptors).

The ligands identified by the methods described herein may be used as targeting agents for delivering therapeutic agents into cells or tissues. For example, a therapeutic gene can be incorporated into the phage genome and delivered to cells via phage bearing the gene delivery ligand on its protein coat.

A transducing gene, as used herein, refers to a gene which encodes a detectable product in the target cell. Preferentially, the transducing gene is a therapeutic gene. A "therapeutic nucleic acid" or "therapeutic gene" describes any nucleic acid molecule used in the context of the invention that effects a treatment, generally by modifying gene transcription or translation. It includes, but is not limited to, the following types of nucleic acids: nucleic acids encoding a protein, ribozyme, antisense nucleic acid, DNA intended to form triplex molecules, protein binding nucleic acids, and small nucleotide molecules. As such, the product of the therapeutic gene may be DNA or RNA. These gene sequences may be naturally-derived sequences or recombinantly derived. A therapeutic nucleic acid may be used to effect genetic therapy by serving as a replacement for a defective gene, by encoding a therapeutic product, such as TNF, or by encoding a cytotoxic molecule, especially an enzyme, such as saporin. The therapeutic nucleic acid may encode all or a portion of a gene, and may function by recombining with DNA already present in a cell, thereby replacing a defective portion of a gene. It may also encode a portion of a protein and exert its effect by virtue of co-suppression of a gene product.

As discussed above, the therapeutic gene is provided in operative linkage with a selected promoter, and optionally in operative linkage with other elements that participate in transcription, translation, localization, stability and the like.

The therapeutic nucleotide composition of the present invention is from about 20 base pairs to about 100,000 base pairs in length. Preferably the nucleic acid molecule is from about 50 base pairs to about 50,000 base pairs in length. More preferably the nucleic acid molecule is from about 50 base pairs to about 10,000 base pairs in length. Even more preferably, it is a nucleic acid molecule from about 50 pairs to about 4,000 base pairs in length.

The ligands/anti-ligands provided herein are useful in the treatment and prevention of various diseases, syndromes, and hyperproliferative disorders, such as restenosis, other smooth muscle cell diseases, tumors, such as melanomas, ovarian cancers, neuroblastomas, pterygii, secondary lens clouding, and the like. As used herein, "treatment" means any manner in which the symptoms of a condition, disorder or disease are ameliorated or otherwise beneficially altered. Treatment also encompasses any pharmaceutical use of the compositions herein. As used herein, "amelioration" of the symptoms of a particular disorder refers to any lessening, whether permanent or temporary, lasting or transient, that can be attributed to or associated with administration of the composition.

In certain embodiments, the compositions of the present invention may be used to treat angiogenesis-dependent diseases. In these diseases, vascular growth is excessive or allows unwanted growth of other tissues by providing blood supply. These diseases include angiofibroma, arteriovenous malformations, arthritis, atherosclerotic plaques, corneal graft neovascularization, delayed wound healing, diabetic retinopathy, granulations due to burns, hemangiomas, hemophilic joints, hypertrophic scars, neovascular glaucoma, nonunion fractures, Osler-weber syndrome, psoriasis, pyogenic granuloma, retrolental fibroplasia, scleroderma, solid tumors, trachoma, and vascular adhesions.

By inhibiting vessel formation (angiogenesis), unwanted growth may be slowed or halted, thus ameliorating the disease. In a normal vessel, a single layer of endothelial cells lines the lumen, and growth of the vessel requires proliferation of endothelial cells and smooth muscle cells.

As well, the ligands, anti-ligands, and cells identified by the present invention may be used to treat tumors. In these diseases, cell growth is excessive or uncontrolled. Tumors suitable for treatment within the context of this invention include, but are not limited to, breast tumors, gliomas, melanomas, prostate cancer, hepatomas, sarcomas, lymphomas, leukemias, ovarian tumors, thymomas, nephromas, pancreatic cancer, colon cancer, head and neck cancer, stomach cancer, lung cancer, mesotheliomas, myeloma, neuroblastoma, retinoblastoma, cervical cancer, uterine cancer, and squamous cell carcinoma of skin. For such treatments, ligands are chosen to bind to cell surface receptors that are generally preferentially expressed in tumors.

Through delivery of the compositions of the present invention, unwanted growth of cells may be slowed or halted, thus ameliorating the disease. The methods utilized herein specifically target and kill or halt proliferation of tumor cells having receptors for the ligand on their surfaces.

The identified ligands/anti-ligands may also be used to treat or prevent atherosclerosis and stenosis, a process and the resulting condition that occurs following angioplasty in which the arteries become reclogged. Generally, treatment of atherosclerosis involves widening a stenotic vascular lumen, permitting greater blood flow and oxygenation to the distal tissue. Unfortunately, these procedures induce a normal wound healing response in the vasculature that results in restenosis. Of the three components to the normal vascular response to injury, thrombosis, elastic recoil and smooth muscle cell proliferation, anti-thrombotics/platelet inhibitors and vascular stents effectively address acute/subacute thrombosis and elastic recoil, respectively. However, no existing therapy can modify the vascular remodeling that is due to proliferation of smooth muscle cells at the lesion, their deposition of extracellular matrix and the subsequent formation of a neointima. Accordingly, phage could be used to deliver therapeutic nucleic acids or proteins that would inhibit restenosis.

Wound response also occurs after other interventions, such as balloon angioplasty of coronary and peripheral vessels, with or without stenting; carotid endarterectomies; vein grafts; and synthetic grafts in peripheral arteries and arteriovenous shunts. Although the time course of the wound response is not well defined, if the response can be suppressed for a short term (approximately 2 weeks), a long term benefit is achieved.

The present invention provides the capability of identifying proteins, antibodies, cell/cell interacting proteins that define the interrelationships between cells, host/pathogen, tumor/stroma, autocrine/paracrine factors and allows identification of molecules that are targets for new drug discovery or are themselves therapeutically or diagnostically useful.

The following examples are offered by way of illustration, and not by way of limitation.

EXAMPLES

Example 1

Modified Phage Vectors for Mammalian Cell Transduction

A mammalian expression cassette is inserted into a phage or phagemid vector and is used to detect ligand mediated phage entry via reporter gene expression in mammalian cells. A type 3 filamentous phage vector is modified for transduction of mammalian cells by insertion of a GFP expression cassette consisting of a CMV mammalian transcriptional promoter, the green fluorescent protein gene from pEGF-PN1 (Clontech; Palo Alto, Calif.), and a bovine growth hormone transcriptional terminator and polyadenylation signal to make the vector, MEGFP3 (see FIG. 1A). The mammalian expression cassette also contains an SV40 origin of replication adjacent to the CMV promoter. Similar constructs for monitoring entry and subsequent expression of phage genomes in mammalian cells are constructed from other known phage or phagemid vectors including pCANTAB 5 E (Pharmacia Biotech; Piscataway, N.J.) or M13 type 3 or 33 for gene III fusions (see Kay et al., *Phage Display of Peptides and Proteins: A Laboratory Manual*, Academic Press, 1996; McConnell et al., *Mol. Divers.* 1:165–176,1996) and M13 type 8 or 88 vector for fusions to gene VIII protein (Roberts et al., *Methods Enzymol.* 267:68–82, 1996; Markland et al., *Gene* 109:13–19, 1991).

Example 2

Construction of FGF2-Containing Phage Display Vectors

Figure 1B:
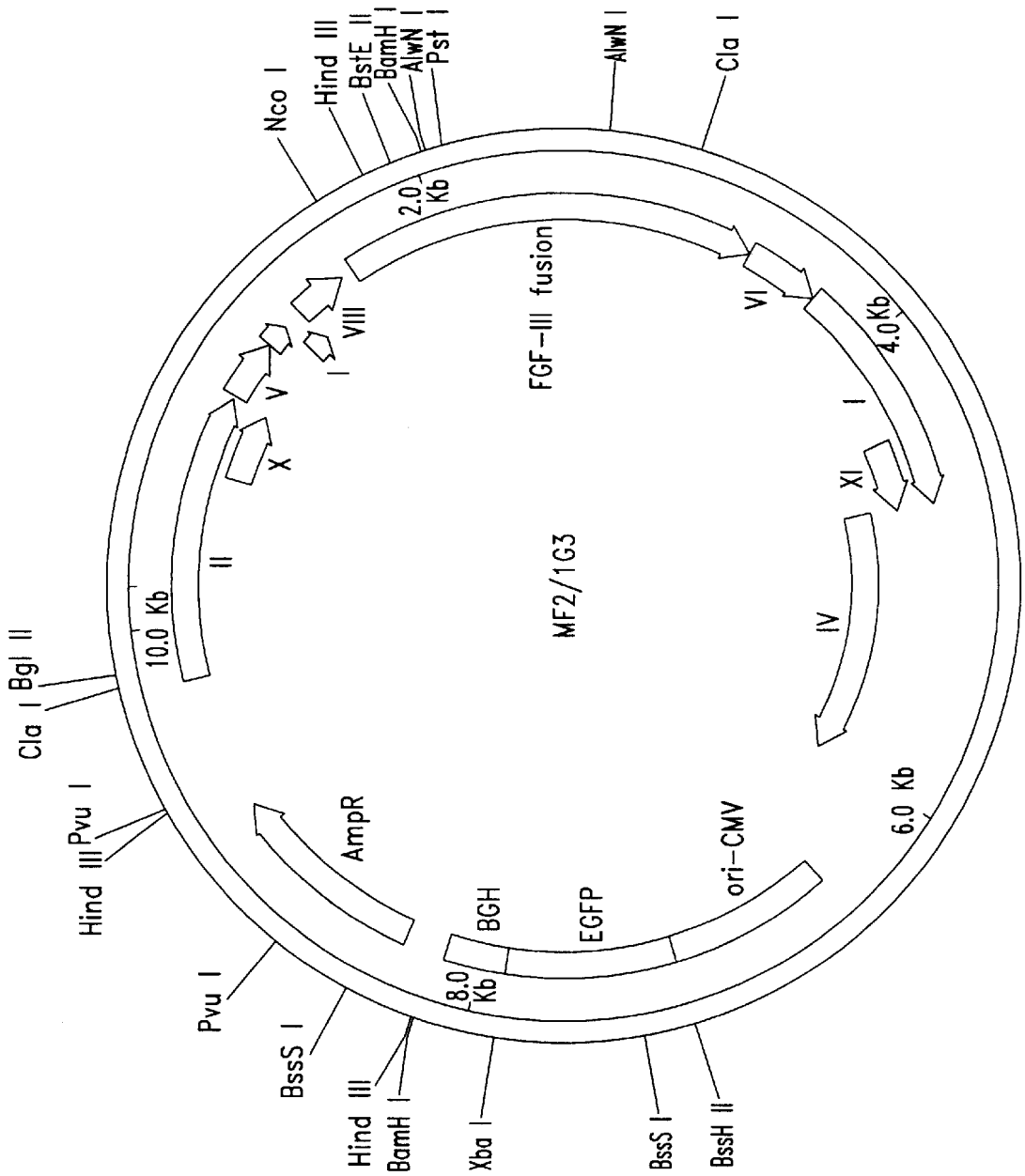

In the following examples, a phage that displays FGF2 on its surface is used to bind to the FGF2 receptor on mammalian cells and be internalized. An FGF2 gene is subcloned into the modified M13 phage type 3 vector, MEGFP3, to create the ligand display phage, MF2/1G3 (see FIG. 1B). The gene may also be mutated such that it encodes an FGF2 (C96S) (C78S) double mutant which enhances expression efficiency. The MEGFP3 vector has been modified with a mammalian expression cassette designed to express the reporter gene GFP to monitor mammalian cell transduction by the phage. Other vectors include pCANTAB 5 E (Pharnacia Biotech; Piscataway, N.J.) or M13 type 3 or 33 for gene III fusions (see Kay et al., *Phage Display of Peptides and Proteins: A Laboratory Manual*, Academic Press, 1996; McConnell et al., *Mol. Divers.* 1:165–176, 1996). Similarly, FGF2 is cloned into M13 type 8 or 88 vector for fusion to gene VIII protein (Roberts et al., *Methods Enzymol.* 267:68–82, 1996; Markland et al., *Gene* 109:13–19, 1991).

Figure 2:
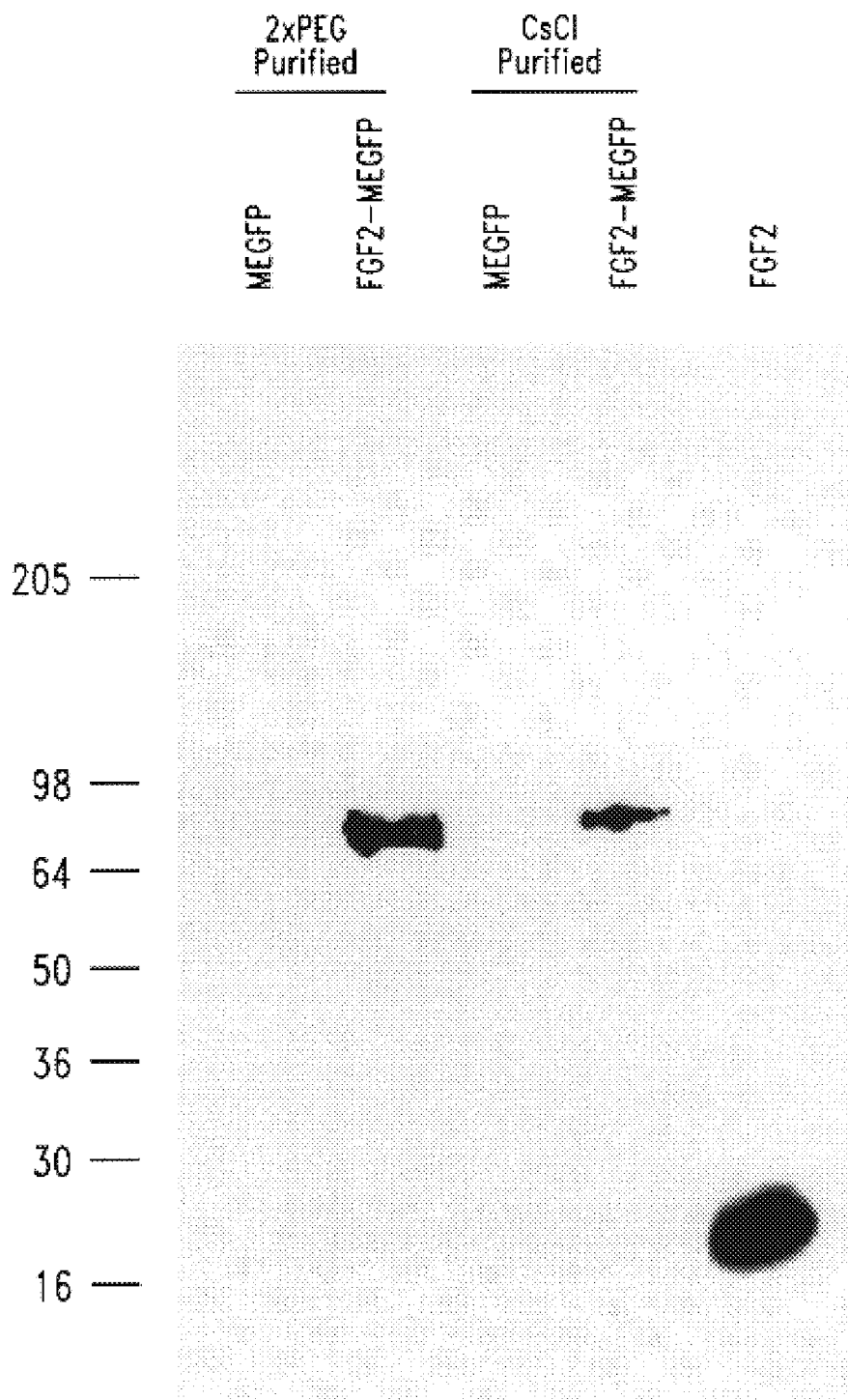
FIG. 2 is a scanned image of a Western Blot analysis representing detection of FGF2-pIII fusion protein in protein extracts from purified FGF2-phage (FGF2-MEGFP).

To facilitate cloning, the FGF2 gene is amplified by PCR using oligonucleotide primers that contain appropriate restriction endonuclease sites in the phage vector gene III or VIII genes. The resulting phage express FGF2 on their surface coat as detected by anti-FGF2 antibodies in Western blots (FIG. 2) and by ELISA (FIG. 3).

Western blot detection of FGF2-pIII fusion utilizes extracts from equivalent phage titers of purified FGF2 phage and control phage (MEGFP3) separated by polyacrylamide gel electrophoresis and blotted onto nitrocellulose. FGF2 and FGF2-fusion phage are detected with an anti-FGF2 monoclonal antibody (Transduction Labs; Lexington, Ky.) and HRP conjugated anti-mouse secondary antibody (American Qualex; San Clemente, Calif.) with chemiluminescent development. A single protein band is detected in the cesium chloride purified FGF2-phage extract migrating at about 80 kDa. This is about the size predicted for the FGF2-pIII fusion protein (FGF2 (18 kDa) fused to pIII (migrates ~60 kDa)). CsCl purification is performed to remove any non-covalently bound FGF2 fusion protein from the phage particles.

Figure 3A:
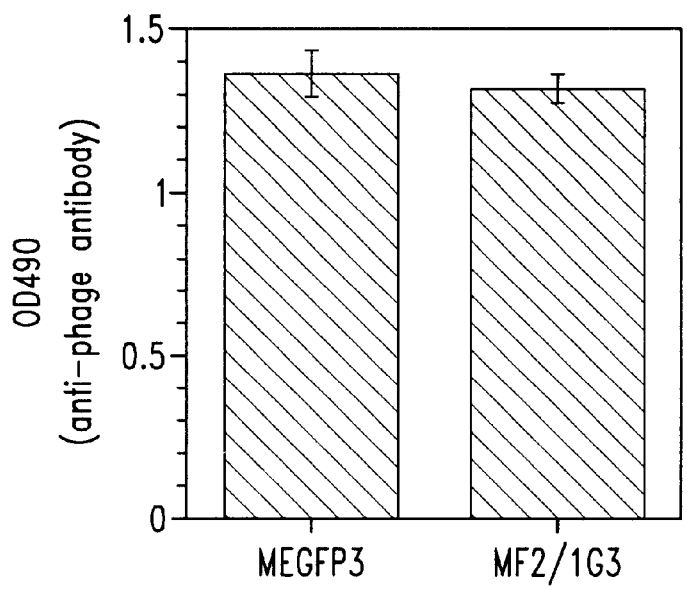
FIGS. 3A and 3B are bar graphs of ELISA detection of FGF2 on FGF2-phage.
Figure 3B:
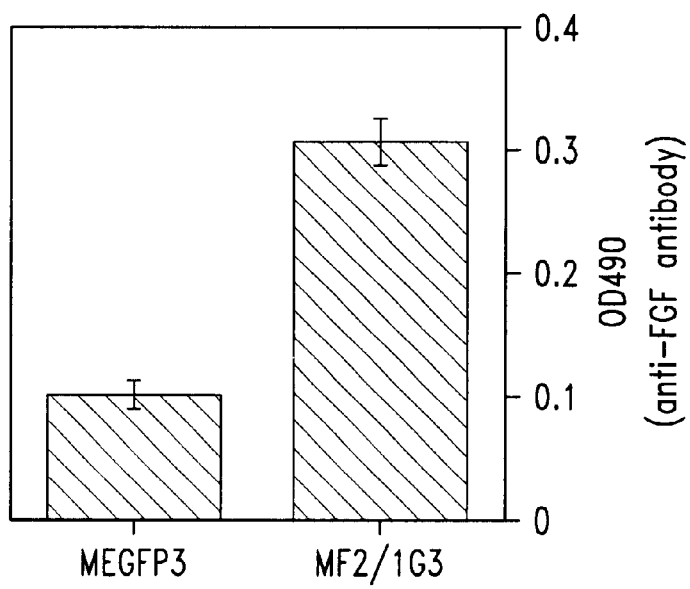

Binding of the FGF2 fusion phage to FGF2 receptor is assessed by ELISA in which recombinant FGF2 receptor is attached to the solid phase and an anti-phage antibody is used as the primary detection antibody. Briefly, phage were captured with an anti-FGF2 rabbit polyclonal antiserum bound to the plate well. An HRP conjugated anti-M13 antibody (Pharmacia Biotech; Piscataway, N.J.) was used to detect the bound phage. When anti-phage antibody is used to capture the phage and equivalent OD is observed for both control (MEGFP3) and FGF2-phage (MF2/1G3) indicating that equivalent phage particles are applied to the plate (FIG. 3A). In FIG. 3B an increased OD indicates the presence of FGF2 on the MF2/1G3 FGF2-phage.

Example 3

Target Cell Line Engineering

To increase the sensitivity of the assay for transduction by ligand display phage the target cell line is transfected with a plasmid that is designed to express the SV40 large T-antigen (i.e. pSV3neo). This plasmid also contains a drug selection gene such as neomycin phosphotransferase (neo) which confers resistance to the antibiotic G418 in stabley transfected mammalian cells. Following transfection of the target cell line with plasmid DNA using standard methods (i.e. $CaPO_4$ co-precipitation) the cells are split and maintained in G418 containing media until drug resistant colonies appear. The colonies are expanded to test for SV40 T-antigen synthesis by western blotting or immunoprecipitation using a suitable antibody. Examples of T-antigen expressing target cell lines are: BOS (BHK with SV40 T-Ag) for screening FGF variants; HOS-116 (HCT116 with SV40 T-Ag) for screening peptides that target human colon carcinoma; AOS-431 (A431 with SV40 T-Ag) for screening EGF variants (all parent cell lines are available from ATCC, Manassas, Va.)

Example 4

Binding and Internalization of FGF2-Expressing Phage

The FGF2-expressing phage are also assayed for high affinity receptor binding and internalization in receptor bearing cells by immunolocalization and fluorescence microscopy (Hart, *J. Biol. Chem.* 269:12468–12474, 1994; Barry et al., *Nature Med.* 2:299–305, 1996; Li, *Nature Biotech.* 15:559–563, 1997).

Infection of mammalian cells with FGF2-expressing phage is performed under conditions that block entry of wild type M13 phage into cells except chloriquine is not used (Barry et al., supra). Phage are added directly to cells at titers of $\leq 10^{10}$ CFU/ml in PBS with 0.1% BSA or other suitable blocking agents and incubated at 37° C. or on ice for at least 1 hour. The cells are then washed extensively in PBS, fixed in 2% paraformaldehyde, and permeabilized in 100% methanol at room temperature for 10 minutes. Cells are incubated with rabbit anti-M13 antibody (Sigma; St. Louis, Mo.) in PBS/BSA for 1 hour. The primary antibody is detected with a phycoerythrin labeled anti-rabbit antibody (Life Technologies (Gibco BRL); Rockville, Md.). Surface bound (incubated on ice) or internalized (37° C. incubation) phage are detected by fluorescence microscopy.

Example 5

Transductiol of Mammalian Cells by FGF2-Ligand Display Phage

Figure 4A:
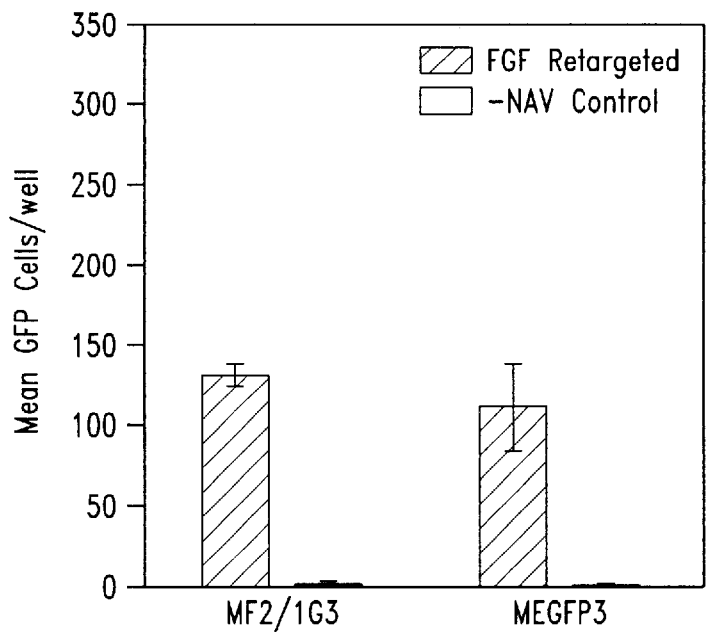
FIGS. 4A and 4B are bar graphs representing the transduction of COS cells by FGF2-phage.
Figure 4B:
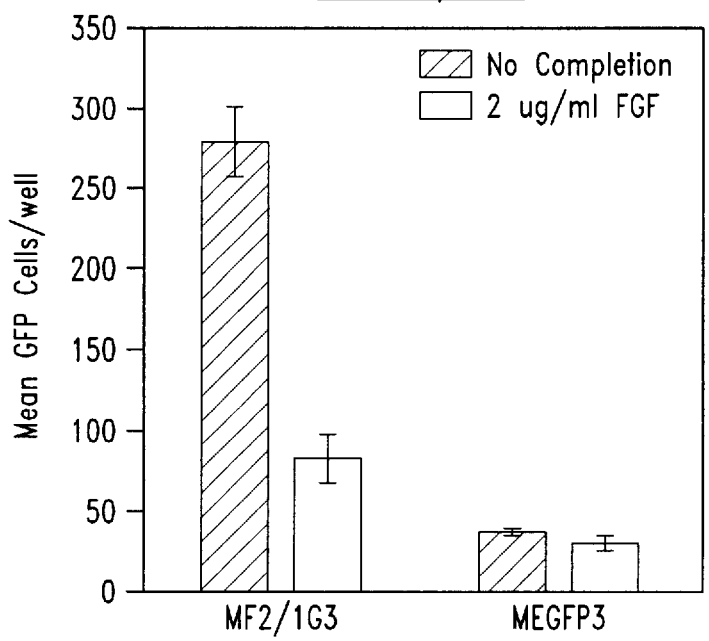

FGF2 display phage (MF2/1G3) and an identical phage that lacks the FGF2 gene (MEGFP3) are compared for receptor mediated internalization and reporter gene expression in COS cells. The phage are incubated with the cells for 4 hours at 37° C. in DME (Dulbecco's modified Eagles medium, Life Technologies (Gibco BRL); Rockville, Md.) containing 2% BSA (bovine serum albumin) as a blocking agent. After washing to remove unbound phage the cells are returned to the incubator for an additional 72 hours. Transduction is measured by counting GFP positive autofluorescent cells. As shown in FIG. 4B, the FGF2 display phage result in about a 10 fold greater transduction efficiency than the control phage indicating that the displayed FGF2 ligand on the surface of the phage particles results in receptor mediated binding and internalization of phage with subsequent expression of the phage reporter gene. The specificity of the FGF2-phage mediated transduction is demonstrated by successful inhibition of transduction with excess free FGF2 (2 μg/ml) (FIG. 4B). The low level nonspecific uptake and transduction by the control phage (MEGFP3) is not affected by the presence of excess FGF2.

It is important to show that the MEGFP3 control phage is equally capable of transducing mammalian cells as the display phage when appropriately targeted. To compare the transduction ability of both the FGF2-phage and the control phage, equivalent titers of each phage were used to transfect COS cells using a avidin-biotin FGF2 targeting method. In this method biotinylated FGF2 is contacted with the cells and used to capture phage particles via the addition of avidin and a biotinylated anti-phage antibody. The phage/FGF2/cell binding is performed on ice, unbound phage removed by washing, cells returned to the incubator at 37° C., and transduction assessed at 72 hours. As seen in FIG. 4A, there is no significant difference in transduction between FGF2-phage and control phage when FGF2 is attached to the phage via an avidin biotin linkage. In this case the biotinylated FGF2 is in excess of the FGF2 displayed on the phage surface such that internalization is expected to be primarily via the biotinylated FGF2. These data demonstrate specific receptor mediated transduction of mammalian cells by filamentous phage that genetically display a targeting ligand (FGF2).

Example 6

Constructio of a Reporter Gene and a Drug Resistance Gene in Phage Display Vectors A GFP expression cassette consisting of the GFP gene (Cormack et al., *Gene* 173:33–37, 1996) under control of a CMV promoter, a neomycin phosphotransferase gene under control of the SV40 early gene promoter, and an SV40 origin of replication are cloned into a gene III phagemid vector such as pCANTAB 5E using standard methods (Sambrook et al., *Molecular Cloning: A Laboratory Manual*, Cold Spring Harbor Press, 1989). The resulting phage is designated pmaM13. The same phagemid genome also containing FGF2–3 fused to gene III is designated pFGF-maM13. Similar constructs are also made with M13 phage type3 and type 33 and gene VIII phagemid and phage vectors. Recombinant phage displaying FGF2 on the coat and carrying the mammalian expression cassettes including the SV40 replication origin are prepared by phagemid rescue with M13K07 (or suitable helper phage) are added to COS cells as described above. GFP expression is detected by fluorescence microscopy, fluorometry, and flow cytometry at 48–96 hours after phage addition. Drug resistant cells are selected with G418.

Example 7

Selection of FGF2-Expressing Phage From a Mixed Population

A M13 phage display library of random or unknown sequences is spiked with pFGF-maM13 phage. The mixture is used to infect COS cells as described above. The cells are washed extensively to remove non-specifically bound phage. Cells are replated 48–96 hours later at a 1 to 10 dilution and grown in G418 to select only cells that receive the transducing phage gene. Alternatively, the GFP expressing cells are isolated by flow cytometry using an excitation wavelength of 488 and emission wavelength of 510.

DNA is extracted from G418-resistant cells and the FGF2 sequence is amplified. The amplification primers have sequences complementary to phage sequences located on each side of the FGF2 sequence in the gene III coding sequence. Detection of the FGF2 sequences in selected COS cells that are infected with a mixture of phage where the pFGF-maM 13 phage is diluted at least 1:10,000 with the random sequence phage library demonstrates feasibility of the technique.

Example 8

Identification of FGF2 Variants for Improved Gene Delivery

A library of shuffled FGF2 mutants is created using the gene shuffling method described by Stemmer (supra). The FGF2 gene is amplified by PCR and fragmented by DNAse 1 treatment. The fragments are reassembled using PCR in the absence of primers. The reassembled gene is cut with the appropriate restriction enzymes and cloned into an M13 phage vector such that the FGF mutants are fused in-frame with the pII coat protein gene. The phage vector contains a CMV promoter driven GFP reporter gene and an SV40 origin of replication. Several individual phage clones are sequenced to confirm that an average of 3 mutations per phage have been generated during the reassembly process. The resulting phage library of FGF2 mutations is amplified by standard protocols. The target cell line, BOS (BHK with T-Ag) is incubated with the library such that each member of the library is at an m.o.i. of at least 10. Accordingly, $10^{11}$ phage representing $10^6$ copies of $10^5$ individual phage species are applied to $10^5$ cells. The phage are incubated with the cells in PBS supplemented with 2% fetal bovine serum for 1–3 hours, after which non-binding phage are removed by extensive washing with PBS. Media is added and the cells returned to the incubator at 37° C. to allow phage internalization.

Example 9

Screening Libraries for Gene Delivery Ligands

If the source of the desired ligand is not known, random peptide libraries or a cDNA library from placenta is used as a starting point for cDNA library screening. The library is amplified in the maM13–33 phage by infecting DH5αF' (or other suitable host) bacteria, growing the culture overnight at 37° C. and isolating the phage from the culture medium using standard protocols. A cDNA library containing $10^5$ members has each member represented $10^6$ times in a typical phage titer of $10^{11}$ colony forming units/ml. The amount of phage used to infect is adjusted to the complexity of the library.

The completed maM13 phage library is screened against the target tissue or cell line. Screening can be performed in-vitro or in-vivo. The criteria for a positive "hit" is that the phage must be able to bind, be internalized, translocate to the nucleus, uncoat and replicate and express the genomic DNA containing the reporter gene in the target cell. Thus, only transduced target cells are selected either by GFP expression and cell sorting or drug resistance. Screening is performed directly against the target cells with no prescreening or enrichment. Enrichment for cell binding is performed if no hits are found in the initial screen. A prescreen to select out phage that bind non-specific cells surface proteins is performed to reduce non-specific hits or if there are too many initial hits. Infection of at least $10^7$ target cells is performed with at least $10^{11}$ phage. The cells are incubated for at least 2 hours in PBS and washed extensively as described by Barry (Barry et al., *Nature Med.*, 2:299–305, 1996). The cells are incubated in media at 37° C. for 48–96 hours and selected in the appropriate drug (e.g., G418) for 7–14 days or until resistant colonies are visible microscopically. Drug resistant colonies are pooled, and the selected cDNAs amplified and subcloned back into the maM13–33 phage vector using PCR and standard molecular biology methods. Alternatively individual colonies are screened. Representative phage clones are sequenced to identify potential gene delivery ligands. Repeated rounds of infection and selection are performed to reduce the complexity of the selected clones. More stringent screening conditions such as increased selective drug concentrations or FACS sorting or the strongest fluorescent cells are performed in the later screens to select the most highly efficient gene delivery ligands from the initial screening.

Screening in-vivo is performed using methods previously described by Pasqualini for targeting organs or xenograft tumors using phage displayed peptides (Pasqualini, R. et al., *Nature Biotechnology*, 15, 542–546 (1997); Pasqualini, R. et al., *Nature*, 380, 364–366 (1996)) except that the organs or tumors are examined for reporter gene expression instead of the presence of phage. The phage library is injected intravenously into mice and organs or tumor samples tested for reporter gene function at 48–96 hours after injection. Tumor cells are cultured in G418 or FACs sorted (for GFP expression) to enrich for cells that express the phage transducing gene. The ligand encoding sequences are amplified from selected cells using PCR as described for in-vitro screening. As in in-vitro screening, repeated rounds of infection and rescreening are performed at increasing screening stringency to obtain the most efficient gene delivery ligands.

Example 10

Identification of Ligands That Target Colon Carcinoma

In this example, a library of oligonucleotides encoding random peptides is inserted into a filamentous phage genome such that the peptides are fused to the C-terminus of intact pIII coat proteins. A type 3 phage vector that only contains one copy of the pIII gene is used and, therefore, all of the pIII protein that is made will be fused to a peptide. Thus, 3–5 copies of a peptide is displayed on each phage. To simplify the screening the complexity of the library is first reduced by screening it for internalizing peptides. Peptides that facilitate the internalization of phage into a colon carcinoma cell line are isolated through several rounds of selection. The phage library is incubated with the cells for 3 hours at room temperature. The cells are washed extensively in PBS. A brief proteinase K treatment is used to inactivate phage that adhere to the cell surface. The cells are then lysed and cell lysates incubated with host bacteria. Internalized phage are amplified in bacteria and subjected to 4 or more iterations of exposure to cells and recovery of internalized phage. Replicative form DNA is prepared from the resulting sublibrary of internalizing phage. The random sequences in the sublibrary are subcloned into a phage vector MEGFP2 that contains a copy of the CMV driven reporter gene (GFP) and an SV40 replication origin. MEGFP2 differs from MEGFP3 (FIG. 1A) in that the ori-CMV/EGFP expression cassette is in the reverse order. EGFP is followed by an SV40 polyadenylation site instead of Bovine Growth Hormone poly A, and the vector contains three additional Nco I sites within the ori-CMV/EGFP expression cassette.

The resulting CMV-GFP modified sublibrary is incubated with the HOS-116 recipient cell line such that each member of the library is represented at least $10^6$ times. Thus, for example, a library with $10^5$ members is added to $\sim 10^5$ cells at a titres of $\sim 1 \times 10^{11}$ yielding an m.o.i. for each member of at least 10. The phage are incubated with the cells in PBS supplemented with 2% fetal bovine serum for 1–3 hours. after which non-binding phage are removed by extensive washing with PBS. Media is added and the cells returned to the incubator at 37° C. to allow phage internalization.

Example 11

Recovery of Ligamend Encoding Sequences From Replicative Phage

At 72 hours following the addition of the phage library. The target cells are removed from the plate and sorted for GFP expressing cells by FACS. The positively sorted cells are lysed and treated with proteinase K. The proteins are extracted with phenol/chloroform (24:1 solution) and nucleic acids precipitated in ethanol. The resulting DNA is resuspended in S1 nuclease buffer and treated with S1 nuclease to remove non-replicative single strand phage DNA. The DNA is again extracted with phenol/chloroform, precipitated, and resuspended in polymerase chain reaction buffer. Alternatively, nuclei are prepared from the positive cells, proteinase K treated and the lysate used directly in the PCR reaction. In either case, an equivalent number of negatively sorted cells are treated in parallel and used in the PCR reaction to monitor the enrichment of replicative phage DNA (double-stranded) over non-replicative phage DNA (single stranded) such that there is no phage DNA amplified in the samples from GFP negative cells. If phage DNA is amplified from negatively sorted cells then conditions must be made more stringent for the removal of single stranded phage DNA such as increasing treatment with S1 nuclease or further purification of nuclei through repeated sucrose step gradient purification or other suitable methods known for purification of nuclei (to remove non-replicative phage). These conditions might need to be determined empirically for each cell line and library used.

The phage sequence(s) encoding the ligand peptide is amplified using an appropriate set of oligonucleotide primers that flank the ligand encoding DNA sequence inserts that is fused to the pIII gene. These amplified inserts are recloned into the parent phage vector to create a sub-library of phage enriched now for gene delivery ligands for the target colon carcinoma cell line. Sequencing is performed on representative clones to determine the complexity. The screening process is reiterated until the complexity is reduced sufficiently to identify one or more targeting ligands.

Example 12

Second Generation Screening of Peptides

Peptides are selected which have been previously identified from a random library by one or more panning or screening procedures using conventional vectors and panning methods (see Kay et al., *Phage Display of Peptides and Proteins: A Laboratory Manual*, Academic Press, 1996). The DNA encoding the selected peptides is inserted as a fusion to the pIII coat protein in the MEGFP2 vector containing the GFP reporter gene cassette.

An M13 phage random peptide library is screened for peptides that bind and internalize in an FGF receptor overproducing cell line, Flg37 (an FGFR1 stable transfectant of L6 cells (available from the ATCC; Manassas, Va.) obtained from Dr. Murray Korc, UCI; Irvine, Calif.). In addition, such a cell line may be easily created by those skilled in the art. Following 5 rounds of panning and rescreening the complexity of the library is reduced such that 80% of the phage are represented by a single peptide-pIII fusion. The resulting peptide, FL5, has the sequence FVPDPYRKSR (SEQ ID NO: 1). The same library is also screened against Flg37 cells by selecting infective phage particles that internalize and associate with nuclei and cytoskeletal proteins. The 2 predominant peptide sequences identified by this screen after 5 rounds of panning are FN5A, CGGGPVAQRC (43%) (SEQ ID NO: 2) and FN5B, CLAHPHGQRC (34%) (SEQ ID NO: 3).

Figure 5:
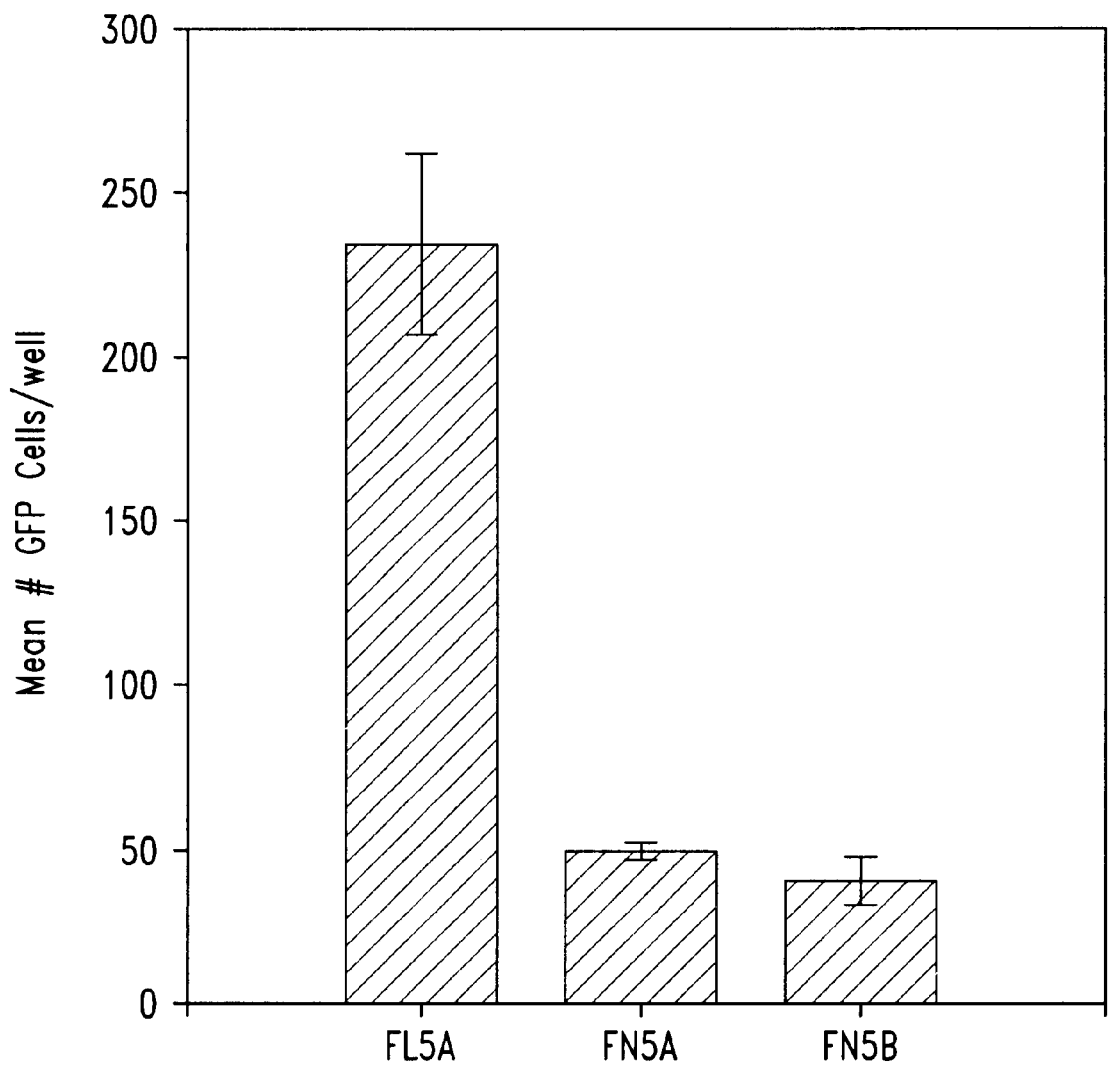
FIG. 5 is a bar graph representing the transduction of COS cells by peptide display phage.

Oligonucleotides encoding the 3 peptides are inserted into the MEGFP vector as fusions to the pIII coat protein. The resulting phage are used to transfect COS cells. Phage are added to cells and incubated overnight at 37° C. in medium with 10% fetal calf serum. The cells are washed to remove unbound phage and returned to the incubator. Transduction is assessed by counting GFP expressing autofluorescent cells at 72 hours after the addition of phage. The results (FIG. 5 are that a greater transduction efficiency is observed with FL5 than FN5A or FN5B indicating that FL5 is a more efficient as a gene transfer ligand in this system. The transduction screening method as a second generation screen is capable of distinguishing among peptides that were selected by different primary cell based screens.

Example 13

EGF Mediated Mammalian Cell Transduction

Figure 6:
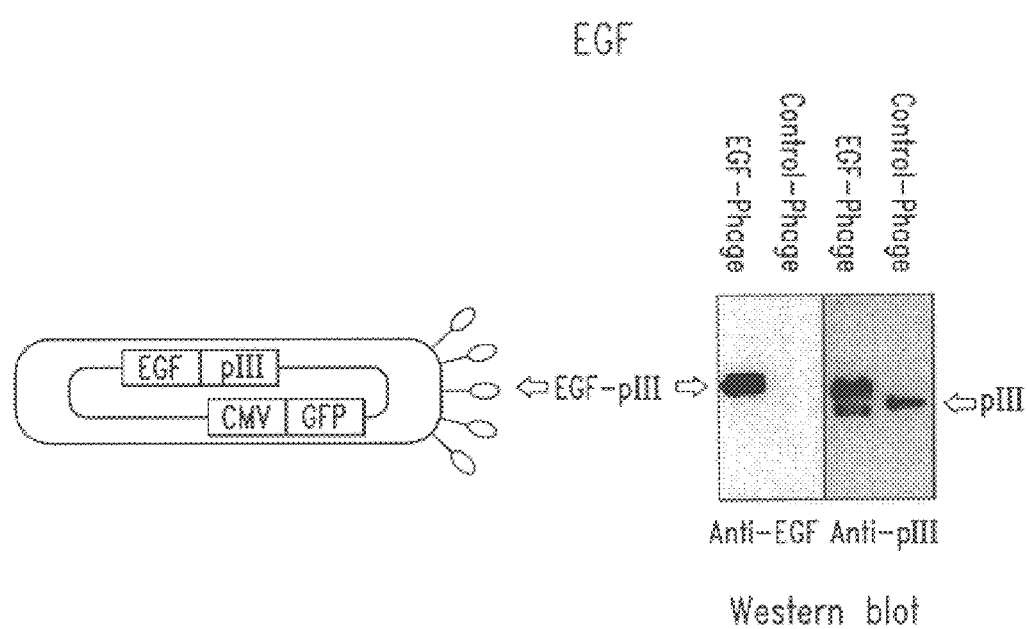
FIG. 6 is a scanned image of a Western Blot analysis representing detection of EGF-pIII fusion protein in protein extracts from purified EGF-phage.

Epidermal growth factor displaying phage were constructed as described above for FGF displaying phage. Western blot analysis demonstrates that EGF was efficiently expressed on the phage coat in a multivalent manner (FIG. 6). Phage were prepared for Western analysis by obtaining the EGF-phage from cultures of infected host bacteria and purified by PEG precipitation and CsCl gradient centrifugation. The phage particle proteins were then separated by gel electrophoresis and blotted onto a nitrocellulose membrane. Blots were then probed with either anti-EGF or anti-pIII antibody (mouse anti-human EGF, Biosource International; Camarillo, Calif.) or anti-pIII antibody (mouse anti-pIII, MoBiTech; Germany) followed by HRP-goat-anti-mouse (Jackson Laboratories, USA).

Figure 7:
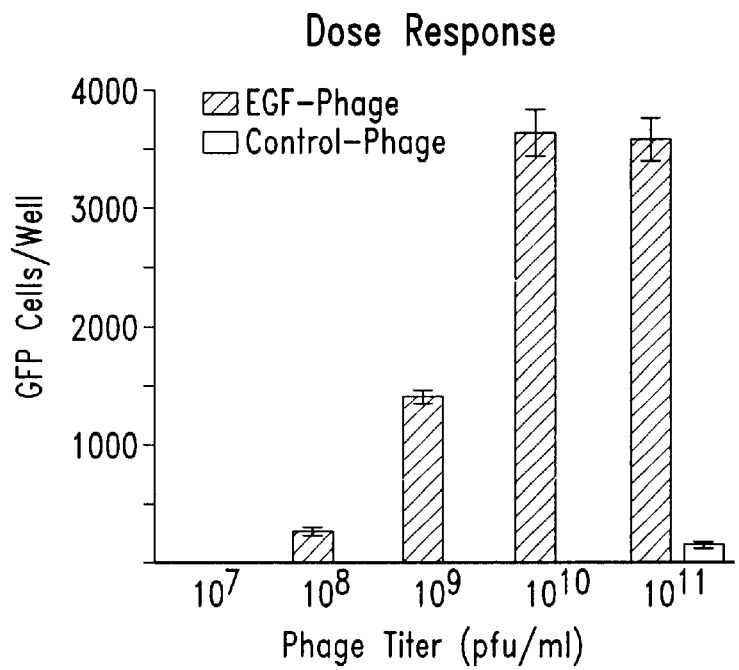
FIG. 7 is a bar graph representing the dose response of COS cells to various phage titers.
Figure 8:
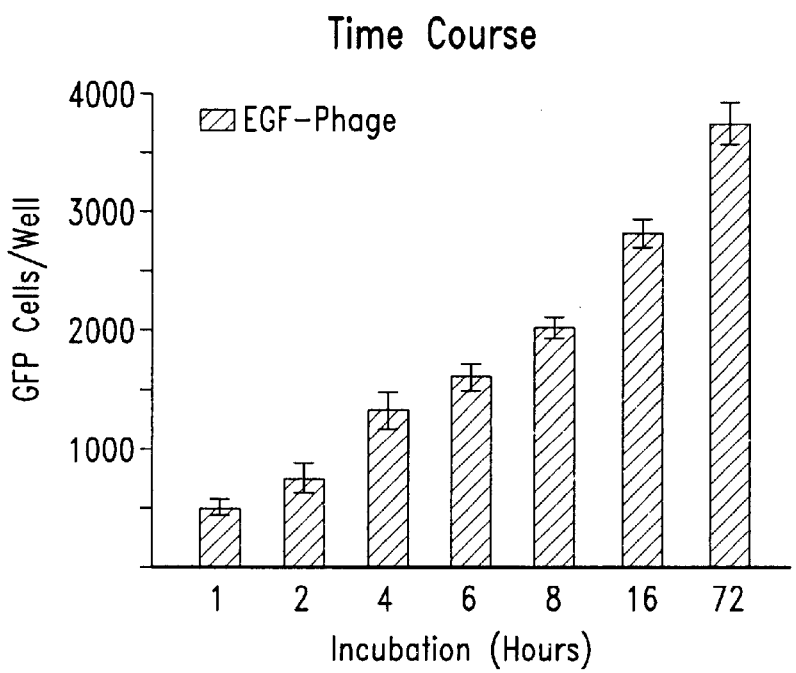
FIG. 8 is a bar graph representing a time course analysis of various incubation times and the effect on transduction.

Following the procedures detailed above, EGF-phage were screened for their ability to effectively transduce COS cells. Briefly, EGF-phage were incubated with COS cells (~75,000 cells/well) for 72 hours with a variety of phage titers. As demonstrated by FIG. 7 the optimal dose was $10^{10}$ pfu/ml which resulted in the highest transduction efficiency with almost no non-specific transduction by untargeted phage. Transduction efficiency also increases with longer incubation times. As demonstrated in FIG. 8 when EGF-phage were incubated with COS cells (~75,000 cells/well) at $10^{11}$ pfu/ml for various times and subsequently measured for GFP expression at 72 hours, longer incubation times increased transduction efficiency.

Figure 9A:
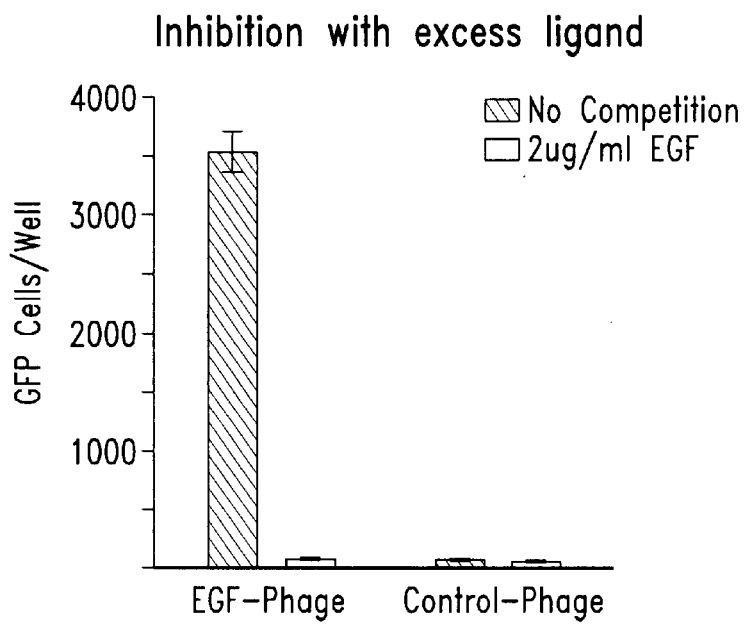
FIGS. 9A and 9B are bar graphs representing the specificity of transduction of COS cells by EGF-phage.
Figure 9B:
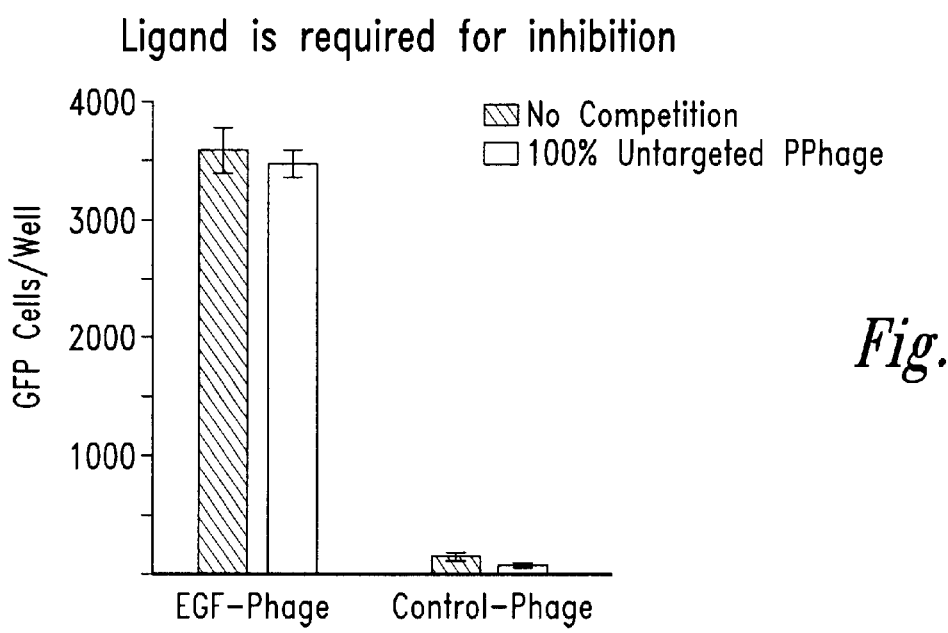

Further, specificity of EGF-phage mediated COS cell transduction was determined by incubating EGF-phage with excess ligand. As depicted in FIGS. 9A and 9B, COS cells incubated with $10_{11}$ pfu/ml of phage for 72 hours with or without excess ligand or untargeted phage demonstrate that targeting is due to the presence of the ligand.

Example 14

Simultaneous Identification of Internalizing Ligands and Anti-ligand Binding Targets To identify internalizing ligand-anti-ligand binding target interactions, the putative ligand is displayed on the surface of filamentous phage that carry a mammalian reporter gene expression cassette. The candidate binding target peptides/proteins are expressed on the surface of COS cells by substituting the target cDNA for the extra cellular domain encoding DNA portion of the EGF receptor in a suitable mammalian cell expression vector (i.e., pcDNA 3.1; Invitrogen, Calif.).

To accomplish this, a library of cDNAs is inserted into a mammalian expression vector (pcDNA 3.1) such that the cDNAs are fused to the transmembranes and intracellular domains of EFG receptor cDNA. DNA is prepared from individual or pools of bacterial clones that have been transformed to carry the cDNA-receptor fusion protein expression plasmid. COS cells are transfected with the resulting plasmid DNAs in six well plates at low density. At 24 hours later, ligand display phage carrying the CMV driven reporter gene GFP are added to the transfected COS cells.

Binding of the phage displayed ligand to the cell surface display binding target (i.e. protein—EGF receptor fusion protein), results in dimerization of the receptor and subsequent internalization of phage that display the binding ligand. The internalized phage are trafficked to the nucleus where the reporter gene is expressed. 72 hours after adding phage, cells expressing the reporter gene are selected by FACs. cDNAs encoding reactive peptides are identified by the presence of GFP positive cells in the COS transfectants for each cDNA or cDNA pool. The binding ligand is identified by PCR amplification and sequencing of the phage ligand-pIII fusion gene. The target peptide is identified by PCR amplification and sequencing the peptide-EGF receptor fusion protein from the selected cell(s).

Example 15

Identification of Cell Targets

Phage that display a ligand as a pIII fusion on the phage coat and carry the GFP expression cassette are prepared using standard protocols, as discussed above. Control phage that carry GFP but don't display a ligand are also prepared. Candidate cell targets are seeded into 6 well culture plates at about 40,000 cells/well. At 24 hours after seeding cells, phage are added at ~$10^{10}$ pfu/ml. The plates are incubated at 37° C. for an additional 72 hours. Each cell well is scored by counting GFP positive autofluorescent cells. The cell types that have a ratio of GFP positive cells in the ligand-phage treated well/control phage treated cells of greater than 1.0 are selected as targets for further study and characterization. As an alternative to GFP, a drug resistance gene can be used in which case after 72 hours the cells are allowed to continue growth in selective medium containing the drug. Positive cell types are scored by counting wells that have drug resistant colonies.

Figure 10:
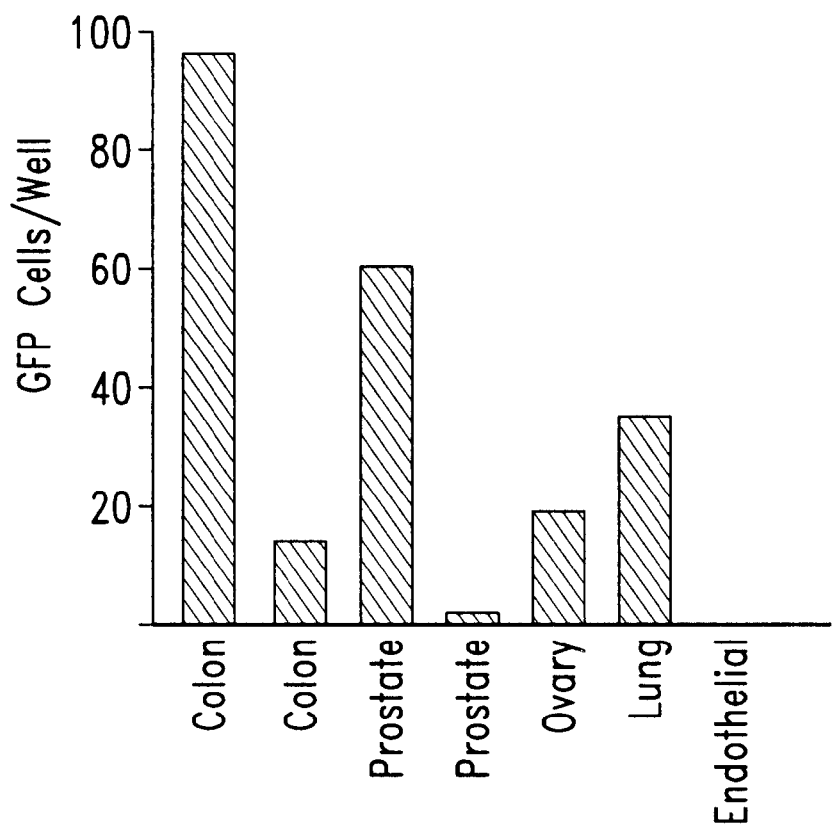
FIG. 10 is a bar graph representing transduction specificity of a variety of human carcinoma cells.

Carcinoma cell lines which are known to express EGF were screened by the above method using EGF-phage and compared to the control endothelial cell line which is EGF receptor negative (Cell lines obtained from ATCC, Manassas, Va. and grown under standard ATCC culture conditions). As shown in FIG. 10, the carcinoma cell lines derived from various tissues were differentially transduced while the receptor negative, endothelial cells displayed no transduction. Accordingly, identification of target cells or tissues can be accomplished using these methods.

Example 16

Identification of Pathogen Target Cells

Ligand display phage are constructed as discussed above, with the ligand being full-length or fragments of coat or envelope proteins of a known or suspected pathogen. The ligand expressed on the display phage coat can be expressed from the cDNA or cDNA derivative of the coat or envelope protein of a known or suspected pathogen (e.g., HIV envelope protein gene). The envelope gene is randomly fragmented to form a library of display phage display distinct portions of the coat protein. Thereby allowing determination of the portion of the gene that encodes a protein that functionally interacts with the host cell surface receptors allowing internalization. Smaller pathogen coat proteins are displayed in entirety. The pathogen coat display phage acts as surrogate pathogen with the advantage of providing a simple assay for detection of host cells. Phage displaying coat protein are screened against various cell types in vitro as described above or in vivo by injection and subsequent identification of target cells and tissues by fluorescent microscopy, FACS analysis to detect GFP, or growth in selective medium to detect expression of a drug resistance marker.

Example 17

Identification of Pathogen Ligands

The gene(s) or portion of a gene that interacts with the host cell surface receptor to allow internalization is identified by making a phage display library of the cDNAs expressed by the pathogen or of the pathogen genome or fragments of the genome. The display library phage vector carries the GFP or suitable reporter gene driven by the mammalian promoter, as described above. The libraries are then screened against a known or putative host cell types by detecting transgene expression (i.e., drug selection or other detectable marker). Once cells are identified, the sequence of the nucleic acid encoding the internalizing ligand is determined by PCR sequencing of the pIII-putative ligand fusion construct.

Example 18

Identification of Secreted and Internalizing Ligands for Tumor Cells

Tumor cells interact with surrounding host stromal and other cell types via chemo-attractants and other factors which, for example, stimulate the stromal cells to secrete factors that support tumor growth (i.e., VEGF). To investigate these interactions, a library of putative secreted ligand cDNAs is prepared tumor cell mRNA and selected by methods known in the art such as epitope-tagging, Sloan et al., *Protein Expression and Purification* 11:119–124, 1997. The secreted protein encoding cDNAs are inserted into the reporter phage vector as described above.

Individual phage clones or pools of phage clones are screened against various stromal cell types to identify cell types that are targets for tumor cell secreted factors, and to identify the secreted factors. The inverse strategy can also be applied by screening a library of, for example, fibroblast or other stromal cell secreted protein encoding cDNAs for factors that bind and internalize into various tumor cell types.

Example 19

Selection of EGF-Expressing Phage From a Population of Non-targeted Phage

Non-targeted M13 phage was spiked with EGF-phage. The mixture was used to infect COS cells and incubated for 72 hours, as described above. The cells are washed extensively to remove non-specifically bound phage. The GFP expressing cells are isolated by flow cytometry (FACS) using an excitation wavelength of 488 and emission wavelength of 510.

DNA is extracted from GFP positive cells and the EGF sequence was amplified by PCR. The amplification primers have sequences complementary to phage sequences located on each side of the EGF sequence in the gene III coding sequence. These sequences were recloned into the phage vector and new phage were prepared for subsequent rounds of selection.

Figure 11:
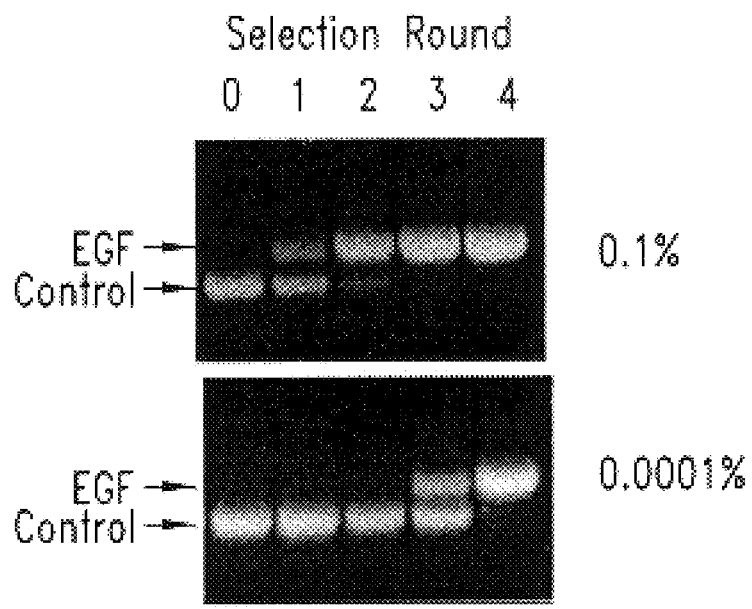
FIG. 11 is a scanned image of ethidium bromide stained gel electrophoretic analysis of products obtained by PCR amplification of pIII genes/pIII gene fusions following various rounds of selection.

As is demonstrated in FIG. 11, enrichment of targeted EGF-phage from 0.1% to 100% EGF-phage was complete after 3 rounds of selection and enrichment from 0.0001% to 100% EGF-phage was complete after 4 rounds of selection. Accordingly, this experiment demonstrates the ability to select a specific ligand expressing phage from a population at dilutions of $1:10^3$ and $1:10^6$. In addition, while further diluted ligand expressing phage can be detected further rounds of selection may be necessary.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method of identifying an internalizing ligand or anti-ligand of an internalizing ligand/anti-ligand pair, comprising:
   (a) contacting one or more ligand displaying genetic packages with a cell(s), wherein the ligand displaying genetic packages comprise a candidate internalizing ligand of an internalizing ligand/anti-ligand pair, wherein the ligand displaying genetic packages carry a gene encoding a detectable product which is expressed upon internalization of the ligand displaying genetic package, and wherein the cell(s) expresses an anti-ligand-receptor fusion protein on its surface;
   (b) detecting the detectable product expressed by the cell(s); and
   (c) recovering a nucleic acid molecule encoding the internalizing ligand and/or a nucleic acid molecule encoding the internalizing anti-ligand from the cell(s) expressing the detectable product, and
      thereby identifying the internalizing ligand and/or anti-ligand of an internalizing ligand/anti-ligand pair.

2. The method of claim 1, further comprising isolating cells that express the detectable product.

3. The method of claim 2, wherein the cells are isolated by flow cytometry.

4. The method of claim 1, wherein the ligand displaying package comprise a library of ligand displaying packages.

5. The method of claim 1, wherein the cells express a library of anti-ligand-receptor fusions.

6. The method of claim 4 or 5, wherein the library is a cDNA library.

7. The method of claim 4 or 5, wherein the library is an antibody gene library.

8. The method of claim 4 or 5, wherein the library is a random peptide gene library.

9. The method of claim 4 or 5, wherein the library is a mutein library.

10. The method of claim 1, wherein the detectable product is selected from the group consisting of green fluorescent protein, β-galactosidase, secreted alkaline phosphatase, chloramphenicol acetyltransferase, luciferase, human growth hormone and neomycin phosphotransferase.

11. The method of claim 1, wherein the ligand displaying genetic packages comprise bacteriophage.

12. The method of claim 11, wherein the bacteriophage are filamentous phage.

13. The method of claim 11 or 12, wherein the bacteriophage carries a genome vector.

14. A method of identifying an internalizing ligand and/or anti-ligand of an internalizing ligand/anti-ligand pair, comprising:
   (a) contacting one or more ligand displaying genetic packages with a cell(s), wherein the ligand displaying genetic packages comprise a candidate internalizing ligand of an internalizing ligand/anti-ligand pair, wherein the ligand displaying genetic packages carry a gene encoding a detectable product which is expressed upon internalization of the ligand displaying genetic package, and wherein the cell(s) expresses an anti-ligand-receptor fusion protein on its surface;
   (b) incubating the cell(s) under selective conditions; and
   (c) recovering a nucleic acid molecule encoding the internalizing ligand and/or a nucleic acid molecule encoding the internalizing anti-ligand from cell(s) which grow under the selective conditions, and
      thereby identifying the internalizing ligand and/or anti-ligand of an internalizing ligand/anti-ligand pair.

15. The method of claim 14, further comprising isolating cells that express the detectable product.

16. The method of claim 15, wherein the cells are isolated by flow cytometry.

17. The method of claim 14, wherein the ligand displaying packages comprises a library of ligand displaying packages.

18. The method of claim 14, wherein the cells express a library of anti-ligand-receptor fusions.

19. The method of claim 17 or 18, wherein the library is a cDNA library.

20. The method of claim 17 or 18, wherein the library is an antibody gene library.

21. The method of claim 17 or 18, wherein the library is a random peptide gene library.

22. The method of claim 17 or 18, wherein the library is a mutein library.

23. The method of claim 14, wherein the ligand displaying package comprises a bacteriophage.

24. The method of claim 23, wherein the bacteriophage are filamentous phage.

25. The method of claim 23 or 24, wherein the bacteriophage carries a genome vector.

\* \* \* \* \*